United States Patent [19]

Stone et al.

[11] Patent Number: 5,786,395
[45] Date of Patent: Jul. 28, 1998

[54] ABSORBENT FOAMS MADE FROM HIGH INTERNAL PHASE EMULSIONS USEFUL FOR ACQUIRING AND DISTRIBUTING AQUEOUS FLUIDS

[75] Inventors: Keith Joseph Stone, Fairfield; Thomas Allen DesMarais, Cincinnati; John Collins Dyer, Cincinnati; Bryn Hird, Cincinnati; Gary Dean La Von, Middletown; Stephen Allen Goldman, Cincinnati; Michelle Renee Peace, Mason; Paul Seiden, Cincinnati, all of Ohio

[73] Assignee: The Procter & Gamble Company, Cincinnati, Ohio

[21] Appl. No.: 689,613

[22] Filed: Aug. 13, 1996

Related U.S. Application Data

[62] Division of Ser. No. 645,664, May 14, 1996, which is a division of Ser. No. 370,695, Jan. 10, 1995, Pat. No. 5,563,179.

[51] Int. Cl.$^6$ ............................................. C08J 9/28
[52] U.S. Cl. ............... 521/64; 428/442.373; 428/314.2; 428/315.7; 428/315.9; 521/62; 521/63; 521/146; 521/149; 604/369
[58] Field of Search ........................... 521/62, 63, 64, 521/146, 149; 428/442.373, 314.2, 315.7, 315.9; 604/369

Primary Examiner—Morton Foelak
Attorney, Agent, or Firm—Eric W. Guttag; Carl J. Roof; E. Kelly Linman

[57] ABSTRACT

Absorbent foams materials that are capable of acquiring and distributing aqueous fluids, especially discharged body fluids such as urine. These absorbent foams combine relatively high capillary absorption pressures and capacity-per-weight properties that allow them to acquire fluid, with or without the aid of gravity. These absorbent foams also give up this fluid efficiently to higher absorption pressure storage materials, including foam-based absorbent fluid storage components, without collapsing. These absorbent foams are made by polymerizing high internal phase emulsions (HIPEs).

11 Claims, 6 Drawing Sheets

ABSORBENT FOAMS MADE FROM HIGH INTERNAL PHASE EMULSIONS USEFUL FOR ACQUIRING AND DISTRIBUTING AQUEOUS FLUIDS

This is a division of application Ser. No. 08/645,664, filed on May 14, 1996, which is a division of application Ser. No. 08/370,695, filed on Jan. 10, 1995 now U.S. Pat. No. 5,563,179.

TECHNICAL FIELD OF THE INVENTION

This application relates to flexible, microporous, open-celled absorbent polymeric foam materials. This application particularly relates to absorbent foam materials made from high internal phase emulsions that are capable of acquiring and distributing aqueous fluids, e.g., urine.

BACKGROUND OF THE INVENTION

The development of highly absorbent articles for use as disposable diapers, adult incontinence pads and briefs, and catamenial products such as sanitary napkins is the subject of substantial commercial interest. The ability to provide high performance absorbent articles such as diapers has been contingent on the ability to develop relatively absorbent cores or structures that can acquire, distribute and store large quantities of discharged body fluids, in particular urine. In this regard, the use of certain particulate absorbent polymers often referred to as "hydrogels," "superabsorbents" or "hydrocolloid" materials has been particularly important. See, for example, U.S. Pat. No. 3,699,103 (Harper et al), issued Jun. 13, 1972, and U.S. Pat. No. 3,770,731 (Harmon), issued Jun. 20, 1972, that disclose the use of such particulate absorbent polymers in absorbent articles. Indeed, the development of high performance diapers has been the direct consequence of thinner absorbent cores that take advantage of the ability of these particulate absorbent polymers to absorb large quantities of discharged aqueous body fluids, typically when used in combination with a fibrous matrix. See, for example, U.S. Pat. No. 4,673,402 (Weisman et al), issued Jun. 16, 1987 and U.S. Pat. No. 4,935,022 (Lash et al), issued Jun. 19, 1990, that disclose dual-layer core structures comprising a fibrous matrix and particulate absorbent polymers useful in fashioning high performance diapers.

These particulate absorbent polymers have previously been unsurpassed in their ability to retain large volumes of fluids, such as urine. A representative example of such particulate absorbent polymers are lightly crosslinked polyacrylates. Like many of the other absorbent polymers, these lightly crosslinked polyacrylates comprise a multiplicity of anionic (charged) carboxy groups attached to the polymer backbone. It is these charged carboxy groups that enable the polymer to absorb aqueous body fluids as the result of osmotic forces.

Absorbency based on capillary forces is also important in many absorbent articles, including diapers. Capillary absorbents can offer superior performance in terms of the rate of fluid acquisition and wicking, i.e. the ability to move aqueous fluid away from the point of initial contact. Indeed, the dual-layer core absorbent structures noted above use the fibrous matrix as the primary capillary transport vehicle to move the initially acquired aqueous body fluid throughout the absorbent core so that it can be absorbed and retained by the particulate absorbent polymer positioned in layers or zones of the core.

Other absorbent materials capable of providing capillary fluid transport are open-celled polymeric foams. Indeed, certain types of polymeric foams have been used in absorbent articles for the purpose of actually imbibing, wicking and/or retaining aqueous body fluids. See, for example, U.S. Pat. No. 3,563,243 (Lindquist), issued Feb. 6, 1971 (absorbent pad for diapers and the like where the primary absorbent is a hydrophilic polyurethane foam sheet); U.S. Pat. No. 4,554,297 (Dabi), issued Nov. 19, 1985 (body fluid absorbing cellular polymers that can be used in diapers or catamenial products); U.S. Pat. No. 4,740,520 (Garvey et al), issued Apr. 26, 1988 (absorbent composite structure such as diapers, feminine care products and the like that contain sponge absorbents made from certain types of super-wicking, crosslinked polyurethane foams).

If made appropriately, open-celled hydrophilic polymeric foams can provide features of capillary fluid acquisition, transport and storage required for use in high performance absorbent cores. Absorbent articles containing such foams can possess desirable wet integrity, can provide suitable fit throughout the entire period the article is worn, and can minimize changes in shape during use (e.g., uncontrolled swelling, bunching). In addition, absorbent articles containing such foam structures can be easier to manufacture on a commercial scale. For example, absorbent diaper cores can simply be stamped out from continuous foam sheets and can be designed to have considerably greater integrity and uniformity than absorbent fibrous webs. Such foams can also be prepared in any desired shape, or even formed into single-piece diapers.

Particularly suitable absorbent foams for absorbent products such as diapers have been made from High internal Phase Emulsions (hereafter referred to as "HIPE"). See, for example, U.S. Pat. No. 5,260,345 (DesMarais et al), issued Nov. 9, 1993 and U.S. Pat. No. 5,268,224 (DesMarais et al), issued Dec. 7, 1993. These absorbent HIPE foams provide desirable fluid handling properties, including: (a) relatively good wicking and fluid distribution characteristics to transport the imbibed urine or other body fluid away from the initial impingement zone and into the unused balance of the foam structure to allow for subsequent gushes of fluid to be accommodated; and (b) a relatively high storage capacity with a relatively high fluid capacity under load, i.e. under compressive forces. These HIPE absorbent foams are also sufficiently flexible and soft so as to provide a high degree of comfort to the wearer of the absorbent article; some can be made relatively thin until subsequently wetted by the absorbed body fluid. See also U.S. Pat. No. 5,147,345 (Young et al), issued Sep. 15, 1992 and U.S. Pat. No. 5,318,554 (Young et al), issued Jun. 7, 1994, which discloses absorbent cores having a fluid acquisition/distribution component that can be a hydrophilic, flexible, open-celled foam such as a melamine-formaldehyde foam (e.g., BASOTECT made by BASF), and a fluid storage/redistribution component that is a HIPE-based absorbent foam.

These foam-based acquisition/distribution components should allow rapid fluid acquisition, as well as efficient partitioning or distribution of fluid to other components of the absorbent core having higher absorption pressures than the desorption pressure of the acquisition/distribution foam. This property of fluid desorption to other core components is important in providing the ability to accept repeated discharges or loadings of fluid and to maintain the skin dryness of the wearer. It also allows the acquisition/distribution foam to serve as a void volume reservoir, or buffer zone, to temporarily hold fluid that can be expressed from the storage components of the core when extraordinarily high pressures are encountered during use of the absorbent article.

In giving this fluid to other core components, these foam-based acquisition/distribution components should do so without densifying or collapsing. Foam-based acquisition/distribution components should also readily accept fluid, with or without the aid of gravity. Foam-based acquisition/distribution components should further provide good aesthetics, be soft and resilient in structure, and have good physical integrity in both wet and dry states.

Accordingly, it would be desirable to be able to make an open-celled absorbent polymeric foam material, in particular an absorbent HIPE foam, that: (1) can function as an acquisition/distribution component in an absorbent core; (2) allows other core components having higher absorption pressures than the desorption pressure of the acquisition/distribution foam to partition away fluid without the acquisition/distribution foam collapsing; (3) keeps the wearer's skin dry, even in "gush" situations and even when subjected to compressive load; (4) is soft, flexible and comfortable to the wearer of the absorbent article; and (5) has a relatively high capacity for fluid so as to provide diapers and other absorbent articles that efficiently utilize core components.

DISCLOSURE OF THE INVENTION

The present invention relates to polymeric foam materials that are capable of acquiring and distributing aqueous fluids, especially discharged body fluids such as urine. These absorbent polymeric foam materials comprise a hydrophilic, flexible, nonionic polymeric foam structure of interconnected open-cells. This foam structure has:

A) the ability to vertically wick synthetic urine to a height of 5 cm in less than about 120 seconds;

B) a capillary absorption pressure (i.e., height at 50% capacity) of from about 5 to about 25 cm;

C) a capillary desorption pressure (i.e., height at 50% capacity) of from about 8 to about 40 cm;

D) a resistance to compression deflection of from about 5 to about 85% when measured under a confining pressure of 0.74 psi;

E) a free absorbent capacity of from about 12 to about 125 g/g.

Besides acquiring and distributing body fluids rapidly, the absorbent foams of the present invention give up this fluid efficiently to other fluid storage components, including foam-based fluid storage components. The absorbent foams of the present invention combine relatively high capillary absorption pressures and capacity-per-weight properties (compared to conventional foams) that allow them to acquire fluid, with or without the aid of gravity. The absorbent foams of the present invention also provide good aesthetics due to their soft, resilient structure and physical integrity. As a result, the absorbent foams of the present invention are particularly attractive for high performance absorbent articles such as diapers, adult incontinence pads or briefs, sanitary napkins, and the like.

A particularly important attribute of the foams of the present invention is that they do not collapse when desorbed by other components in the absorbent core. While not being bound by theory, it is believed that this resistance to compression (i.e., resistance to collapse) by hydrostatic pressures is due to the desorption pressure of these foams in their expanded state being less than the pressure required for compression deflection. A related important attribute is that these foams, when wetted, spontaneously reexpand after application and release of mechanical compression, even if the foams do not reabsorb fluid. This means these foams imbibe air when dewatered by either desorption, by mechanical compression, or a combination thereof, when expanded or when returning to an expanded state. As a result, the capability of these foams to quickly acquire fluids is restored and the foam is able to provide a drier feel.

The present invention further relates to a process for obtaining these absorbent foams by polymerizing a specific type of water-in-oil emulsion or HIPE having a relatively small amount of an oil phase and a relatively greater amount of a water phase. This process comprises the steps of:

A) forming a water-in-oil emulsion at a temperature of about 50° C. or higher and under low shear mixing from:

1) an oil phase comprising:

a) from about 85 to about 98% by weight of a monomer component capable of forming a copolymer having a Tg of about 35° C. or lower, the monomer component comprising:

i) from about 30 to about 80% by weight of at least one substantially water-insoluble monofunctional monomer capable of forming an atactic amorphous polymer having a Tg of about 25° C. or lower;

ii) from about 5 to about 40% by weight of at least one substantially water-insoluble monofunctional comonomer capable of imparting toughness about equivalent to that provided by styrene;

iii) from about 5 to about 25% by weight of a first substantially water-insoluble, polyfunctional crosslinking agent selected from divinyl benzenes, trivinylbenzenes, divinyltoluenes, divinylxylenes, divinylnaphthalenes divinylalkylbenzenes, divinylphenanthrenes, divinylbiphenyls, divinyldiphenylmethanes, divinylbenzyls, divinylphenylethers, divinyldiphenylsulfides, divinylfurans, divinylsulfide, divinyl sulfone, and mixtures thereof; and iv) from 0 to about 15% by weight of a second substantially water-insoluble, polyfunctional crosslinking agent selected from polyfunctional acrylates, methacrylates, acrylamides, methacrylamides, and mixtures thereof; and b) from about 2 to about 15% by weight of an emulsifier component which is soluble in the oil phase and which is suitable for forming a stable water-in-oil emulsion, the emulsion component comprising: (i) a primary emulsifier having at least about 40% by weight emulsifying components selected from diglycerol monoesters of linear unsaturated $C_{16}$–$C_{22}$ fatty acids, diglycerol monoesters of branched $C_{16}$–$C_{24}$ fatty acids, diglycerol monoaliphatic ethers of branched $C_{16}$–$C_{24}$ alcohols, diglycerol monoaliphatic ethers of linear unsaturated $C_{16}$–$C_{22}$ fatty alcohols, diglycerol monoaliphatic ethers of linear saturated $C_{12}$–$C_{14}$ alcohols, sorbitan monoesters of linear unsaturated $C_{16}$–$C_{22}$ fatty acids, sorbitan monoesters of branched $C_{16}$–$C_{24}$ fatty acids, and mixtures thereof; or (ii) the combination a primary emulsifier having at least 20% by weight of these emulsifying components and certain secondary emulsifiers in a weight ratio of primary to secondary emulsifier of from about 50:1 to about 1:4; and 2) a water phase comprising an aqueous solution containing: (i) from about 0.2 to about 20% by weight of a water-soluble electrolyte; and (ii) an effective amount of a polymerization initiator;

3) a volume to weight ratio of water phase to oil phase in the range of from about 12:1 to about 125:1; and B) polymerizing the monomer component in the oil phase of the water-in-oil emulsion to form a polymeric foam material; and C) optionally dewatering the polymeric foam material.

The process of the present invention allows the formation of these absorbent foams that are capable of acquiring and rapidly distributing fluids as a result of a combination of two factors. One is the use of low shear mixing during HIPE formation. The other is the use of more robust emulsifier systems that allow the HIPE to be formed and poured at relatively high temperatures, e.g. about 50° C. or higher.

DETAILED DESCRIPTION OF THE INVENTION

I. Polymeric Absorbent Foams

A. General Foam Characteristics

Figure 1:
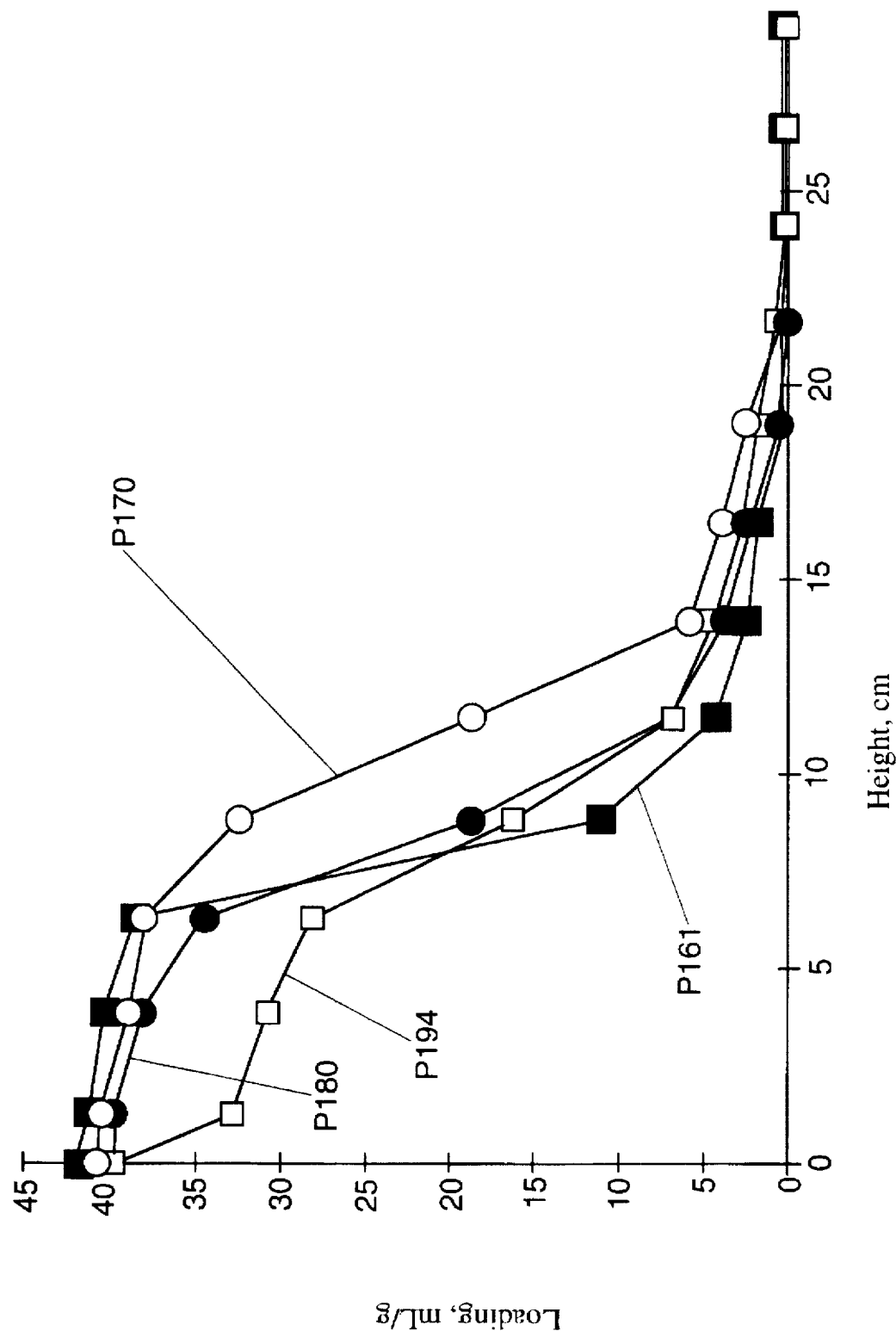
FIG. 1 of the drawings is a graphical plot of the absorption curves of four HIPE foams poured at different temperatures.

Polymeric foams according to the present invention useful in absorbent articles and structures are those which are relatively open-celled. This means the individual cells of the foam are in complete, unobstructed communication with adjoining cells. The cells in such substantially open-celled foam structures have intercellular openings or "windows" that are large enough to permit ready fluid transfer from one cell to the other within the foam structure.

These substantially open-celled foam structures will generally have a reticulated character with the individual cells being defined by a plurality of mutually connected, three dimensionally branched webs. The strands of polymeric material making up these branched webs can be referred to as "struts." Open-celled foams having a typical strut-type structure are shown by way of example in the photomicrographs of FIGS. 3 and 4. For purposes of the present invention, a foam material is "open-celled" if at least 80% of the cells in the foam structure that are at least 1 μm in size are in fluid communication with at least one adjacent cell.

In addition to being open-celled, these polymeric foams are sufficiently hydrophilic to permit the foam to absorb aqueous fluids. The internal surfaces of the foam structures are rendered hydrophilic by residual hydrophilizing surfactants left in the foam structure after polymerization, or by selected post-polymerization foam treatment procedures, as described hereafter.

The extent to which these polymeric foams are "hydrophilic" can be quantified by the "adhesion tension" value exhibited when in contact with an absorbable test liquid. The adhesion tension exhibited by these foams can be determined experimentally using a procedure where weight uptake of a test liquid, e.g., synthetic urine, is measured for a sample of known dimensions and capillary suction specific surface area. Such a procedure is described in greater detail in the TEST METHODS section of copending U.S. application Ser. No. 989,270 (Dyer et al), filed Dec. 11, 1992, which is incorporated by reference. Foams which are useful as absorbents in the present invention are generally those which exhibit an adhesion tension value of from about 15 to about 65 dynes/cm, more preferably from about 20 to about 65 dynes/cm, as determined by capillary suction uptake of synthetic urine having a surface tension of 65±5 dynes/cm.

An important aspect of these foams is their glass transition temperature (Tg). The Tg represents the midpoint of the transition between the glassy and rubbery states of the polymer. Foams that have a higher Tg than the temperature of use can be very strong but will also be very rigid and potentially prone to fracture. Such foams also typically take a long time to respond when used at temperatures colder than the Tg of the polymer. The desired combination of mechanical properties, specifically strength and resilience, typically necessitates a fairly selective range of monomer types and levels to achieve these desired properties.

For foams of the present invention, the Tg should be as low as possible, so long as the foam has acceptable strength. Accordingly, monomers are selected as much as possible that provide corresponding homopolymers having lower Tg's. It has been found that the chain length of the alkyl group on the acrylate and methacrylate comonomers can be longer than would be predicted from the Tg of the homologous homopolymer series. Specifically, it has been found that the homologous series of alkyl acrylate or methacrylate homopolymers have a minimum Tg at a chain length of 8 carbon atoms. By contrast, the minimum Tg of the copolymers of the present invention occurs at a chain length of about 12 carbon atoms. (While the alkyl substituted styrene monomers can be used in place of the alkyl acrylates and methacrylates, their availability is currently extremely limited).

The shape of the glass transition region of the polymer can also be important, i.e., whether it is narrow or broad as a function of temperature. This glass transition region shape is particularly relevant where the in-use temperature (usually ambient or body temperature) of the polymer is at or near the Tg. For example, a broader transition region can mean an incomplete transition at in-use temperatures. Typically, if the transition is incomplete at the in-use temperature, the polymer will evidence greater rigidity and will be less resilient. Conversely, if the transition is completed at the in-use temperature, then the polymer will exhibit faster recovery from compression. Accordingly, it is desirable to control the Tg and the breadth of the transition region of the polymer to achieve the desired mechanical properties. Generally, it is preferred that the Tg of the polymer be at least about 10° C. lower than the in-use temperature. (The Tg and the width of the transition region are derived from the loss tangent vs.

temperature curve from a dynamic mechanical analysis (DMA) measurement, as described in the Test Methods section hereafter).

B. Foam Characteristics Important to Acquiring and Distributing Aqueous Fluids Without Collapsing 1. Vertical Wicking Vertical wicking, i.e., fluid wicking in a direction opposite from gravitational forces, of given amount of fluid within a set period of time is an especially important performance attribute for absorbent foams herein. These foams will frequently be utilized in absorbent articles in a manner such that fluid to be absorbed must be moved within the article from a relatively lower position to a relatively higher position within the absorbent core of the article. Accordingly, the ability of these foams to wick fluid against gravitational forces is particularly relevant to their functioning as fluid acquisition and distribution components in absorbent articles.

Vertical wicking is determined by measuring the time taken for a colored test liquid (e.g., synthetic urine) in a reservoir to wick a vertical distance of 5 cm through a test strip of foam of specified size. The vertical wicking procedure is described in greater detail in the TEST METHODS section of copending U.S. application Ser. No. 989,270 (Dyer et al), filed Dec. 11, 1992, (herein incorporated by reference), but is performed at 31° C., instead of 37° C. To be especially useful in absorbent articles for absorbing urine, the foam absorbents of the present invention will preferably vertically wick synthetic urine (65±5 dynes/cm) 5 cm in no more than about 120 seconds. More preferably, the preferred foam absorbents of the present invention will vertically wick this synthetic urine 5 cm in no more than about 70 seconds, and most preferably in no more than about 50 seconds.

2. Capillary Absorption and Desorption Pressures

Another important property of useful absorbent foams according to the present invention is their capillary absorption pressure. Capillary absorption pressure refers to the ability of the foam to wick fluid vertically. [See P. K. Chatterjee and H. V. Nguyen in "Absorbency," Textile Science and Technology, Vol. 7; P. K. Chatterjee, Ed.; Elsevier: Amsterdam, 1985; Chapter 2.] For the purposes of the present invention, the capillary absorption pressure of interest is the hydrostatic head at which the vertically wicked fluid loading is 50% of the free absorbent capacity under equilibrium conditions at 31° C. The hydrostatic head is represented by a column of fluid (e.g., synthetic urine) of height h. As illustrated in FIG. 1, for foams of the present invention, this is typically the inflection point on the capillary absorption curve.

FIG. 1 depicts the absorption curves for four foams identified as P161, P170, P180 and P194 which correspond to HIPEs poured at 161° F. (72° C.), 170° F. (77° C.), 180° F. (82° C.) and 194° F. (90° C.), respectively. The absorption pressures were determined from these absorption curves and are summarized in Table 1 below:

TABLE 1

| Pour Temperature | Absorption Pressure (cm) |
|---|---|
| 161° F. | 8 |
| 170° F. | 12 |
| 180° F. | 8 |
| 194° F. | 8 |

Figure 2:
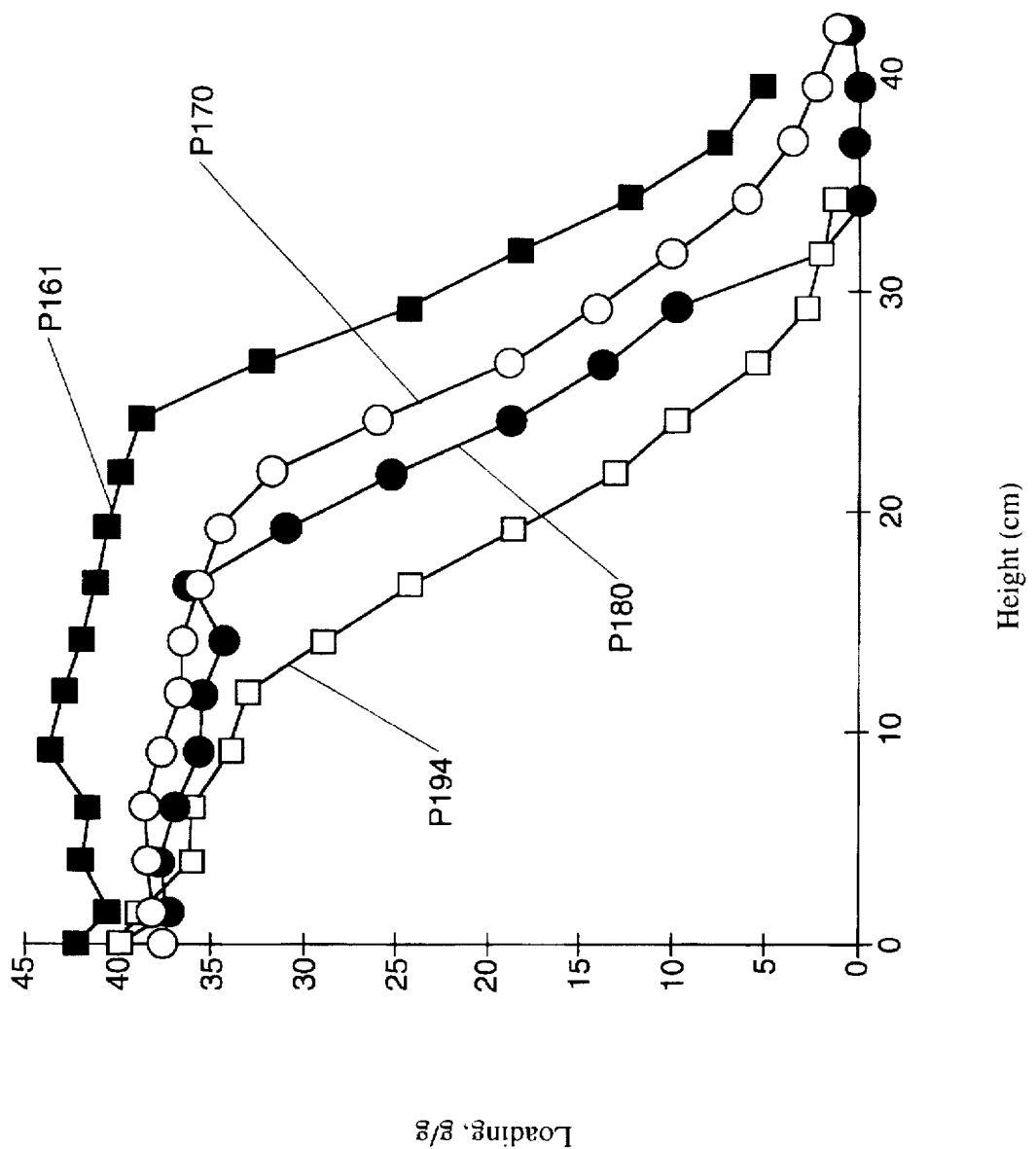
FIG. 2 of the drawings is a graphical plot of the desorption curves of these same four HIPE foams.

Of particular importance to the ability of the absorbent foams of the present invention to function as useful fluid acquisition and distribution components is their capillary desorption pressure. Capillary desorption pressure refers to the foam's ability to hold onto fluid at various hydrostatic heads at equilibrium conditions at 22° C. For the purposes of the present invention, the capillary desorption pressure of interest is the hydrostatic head (i.e., height) at which the fluid loading is 50% of the free absorbent capacity under equilibrium conditions at 22° C. As illustrated in FIG. 2, for foams of the present invention, this is typically the inflection point on the capillary desorption curve.

FIG. 2 depicts the desorption curves of the same four foams identified as P161, P170, P180 and P194 which correspond to HIPEs poured at 161° F. (72° C.), 170° F. (77° C.), 180° F. (82° C.) and 194° F. (90° C.), respectively. The desorption pressures were determined from these desorption curves and are summarized in Table 2 below:

TABLE 2

| Pour Temperature | Desorption Pressure (cm) |
|---|---|
| 161° F. | 31 |
| 170° F. | 27 |
| 180° F. | 24 |
| 194° F. | 19 |

The capillary desorption pressure is important relative to the absorption pressure of other absorbent components, especially those intended for fluid storage. If the fluid acquisition component of the absorbent article holds the acquired fluid too tenaciously, this will inhibit the ability of these other components to partition fluid away. This can cause the acquisition component to remain so heavily loaded with fluid that the absorbent article is more susceptible to leaking. The foams of the present invention have desorption pressures low enough so that fluid storage components can effectively dry out (i.e. desorb) these foams. This restores the capacity of the foam to accept further fluid "gushes" (either from the wearer or from squeeze out from the storage components) and keeps the layer (e.g., topsheet) next to the skin of the wearer comparatively dry. The data in Table 2 above shows how this property can be adjusted by selection of appropriate processing conditions (e.g., pour temperature).

The absorbent foams of the present invention can be readily desorbed by other components of the absorbent core that store such fluids, including those comprising conventional absorbent gelling materials such as are disclosed in, for example, U.S. Pat. No. 5,061,259 (Goldman et. al), issued Oct. 29, 1991, U.S. Pat. No. 4,654,039 (Brandt et al), issued Mar. 31, 1987 (reissued Apr. 19, 1988 as Re. 32,649), U.S. Pat. No. 4,666,983 (Tsubakimoto et al), issued May 19, 1987, and U.S. Pat. No. 4,625,001 (Tsubakimoto et al), issued Nov. 25, 1986, all of which are incorporated by reference; as well as absorbent macrostructures made from these absorbent gelling materials such as those disclosed in, for example, U.S. Pat. No. 5,102,597 (Roe et al), issued Apr. 7, 1992, and U.S. Pat. No. 5,324,561 (Rezai et al), issued Jun. 23, 1994, both of which are incorporated by reference). Indeed, these absorbent foams can be readily desorbed by other absorbent polymeric foams that store the acquired fluid, such as those disclosed in, for example, U.S. Pat. No. 5,268,224 (DesMarais et al), issued Dec. 7, 1993, copending U.S. application Ser. No. 989,270 (Dyer et al), filed Dec. 1992, and copending U.S. application Ser. No. 08/563,866 (Thomas A. DesMarais et al), filed Nov. 29, 1995, Case No. 5541, all of which are incorporated by reference. Accordingly, the absorbent foams of the present invention function very well in multiple "gush" situations to move the acquired fluid rapidly to other fluid storage components of the absorbent structure.

Capillary absorption pressures can be measured using a vertical wicking absorbent capacity test as described in greater detail in the TEST METHODS section of copending U.S. application Ser. No. 989,270 (Dyer et al), filed December 1992, which is incorporated by reference, except at 31° C. rather than 37° C. Data from the vertical wicking absorbent capacity test provides the curve from which the capillary absorption pressure is determined.

Capillary desorption pressure can be measured using the procedure described in the TEST METHODS section. To generate the data for a desorption curve, a foam sample is saturated with water, hung vertically and then allowed to desorb until equilibrium is reached. The fluid loading is then plotted as a function of height. The capillary desorption pressure, i.e., the hydrostatic head at which the fluid loading is 50% of the free absorbent capacity, is determined from this curve.

Suitable absorbent foams according to the present invention have capillary absorption pressures of from about 5 to about 25 cm and capillary desorption pressures of about 8 to about 40 cm. Particularly preferred absorbent foams have capillary absorption pressures of from about 5 to about 15 cm and capillary desorption pressures of about 8 to about 25 cm.

3. Resistance to Compression Deflection

An important mechanical feature of the absorbent foams of the present invention is their strength as determined by their resistance to compression deflection (RTCD). The RTCD exhibited by the foams herein is a function of the polymer modulus, as well as the density and structure of the foam network. The polymer modulus is, in turn, determined by: a) the polymer composition; b) the conditions under which the foam was polymerized (for example, the completeness of polymerization obtained, specifically with respect to crosslinking); and c) the extent to which the polymer is plasticized by residual material, e.g., emulsifiers, left in the foam structure after processing.

To be useful as fluid acquisition/distribution components in absorbent cores of absorbent articles such as diapers, the foams of the present invention must be suitably resistant to deformation or compression by forces encountered when such absorbent materials are engaged in the absorption and retention of fluids. This is particularly important as fluids are partitioned, either due to a sorption pressure gradient or squeeze out, from the acquisition/distribution components and into other fluid storage components in the absorbent core. Indeed, the acquisition/distribution foams of the present invention provide a balance of capillary desorption pressure and foam strength to avoid undesirable collapse during partitioning.

If the capillary desorption pressure of the foam is greater than its RTCD and/or its re-expansion strength (i.e., expansion pressure at a particular % compression), it will tend to collapse upon desorption and thus leave the foam in a saturated, densified state. In this state, the acquisition/distribution foam can feel wet to the touch, leading to wetter skin for the wearer. It would also impede the rate of acquiring additional fluid gushes.

If the foams are too strong, however, they will look and feel stiff, leading to poor aesthetics. Also, one mechanism by which foams of the present invention can distribute and partition fluid involves mechanical pumping. Thus it can be advantageous for the acquisition/distribution foam to be squeezed to some degree by normal pressures experienced by the wearer during use to promote this additional partitioning mechanism.

The RTCD exhibited by the polymeric foams of the present invention can be quantified by determining the amount of strain produced in a sample of saturated foam held under a certain confining pressure for a specified period of time. The method for carrying out this particular type of test is described hereafter in the TEST METHODS section. Foams useful as absorbents for acquiring and distributing fluids are those which exhibit a resistance to compression deflection such that a confining pressure of 0.74 psi (5.1 kPa) produces a strain of typically from about 5 to about 85% compression of the foam structure. Preferably the strain produced under such conditions will be in the range from about 5 to about 65%, most preferably from about 5 to about 50%.

4. Recovery from Wet Compression

Recovery from wet compression (RFWC) relates to the tendency or propensity of a piece of wet foam material to quickly return to its original dimensions after being deformed or compressed under forces encountered in manufacture or use, without having a reservoir of free fluid to draw from during re-expansion. Many high capillary pressure foams, such as those described in U.S. Pat. No. 5,268,224 (DesMarais et al.), issued Dec. 7, 1993, and in copending U.S. application Ser. No. 989,270 (Dyer et al), filed Dec. 11, 1992, will not readily reexpand. It has also been found that re-expansion is even more difficult for an acquisition/distribution foam when it is in competition for fluid with a higher sorption pressure component, such as is typically encountered in absorbent cores.

A suitable procedure for determining recovery from wet compression is set forth in the TEST METHODS section. Such a procedure in general involves compression of a foam sample that has previously been saturated to its free absorbent capacity with synthetic urine while positioned on top of a high capillary absorption pressure material. Samples are maintained under a strain of 75% compression at a constant temperature (31° C.) for a period of five minutes, then are released from compression. After two minutes of competing for the fluid with the higher sorption pressure material (the sample having had the opportunity to re-expand), the sample is separated and its thickness measured. The extent to which the sample recovers its thickness is taken as a measure of the recovery from wet compression of the sample.

Preferred absorbent foams of the present invention will generally exhibit a recovery to at least about 60% of the fully expanded thickness within two minutes of being released from compression. More preferably, such preferred foam materials will have a recovery from wet compression of at least about 75%, most preferably at least about 90%, of the fully expanded thickness within one minute of being released from compression.

5. Free Absorbent Capacity

Another important property of absorbent foams according to the present invention is their free absorbent capacity. "Free absorbent capacity" is the total amount of test fluid (synthetic urine) which a given foam sample will absorb into its cellular structure per unit mass of solid material in the sample. The foams which are especially useful in absorbent articles such as diapers will at least meet a minimum free absorbent capacity. To be especially useful in absorbent articles for absorbing urine, the absorbent foams of the present invention should have a free capacity of from about 12 to about 125 g/g, preferably from about 20 to about 90 g/g, and most preferably from about 45 to about 75 g/g, of synthetic urine per gram of dry foam material. The procedure for determining the free absorbent capacity of the foam is described hereafter in the TEST METHODS section.

C. Other Properties of Polymeric Foam

1. Cell and Hole Sizes

A feature that can be useful in defining preferred polymeric foams is the cell structure. Foam cells, and especially cells that are formed by polymerizing a monomer-containing oil phase that surrounds relatively monomer-free water-phase droplets, will frequently be substantially spherical in shape. These spherical cells are connected to each other by openings, which are referred to hereafter as holes between cells. Both the size or "diameter" of such spherical cells and the diameter of the openings (holes) between the cells are commonly used for characterizing foams in general. Since the cells, and holes between the gels, in a given sample of polymeric foam will not necessarily be of approximately the same size; average cell and hole sizes, i.e., average cell and hole diameters, will often be specified.

Figure 3:
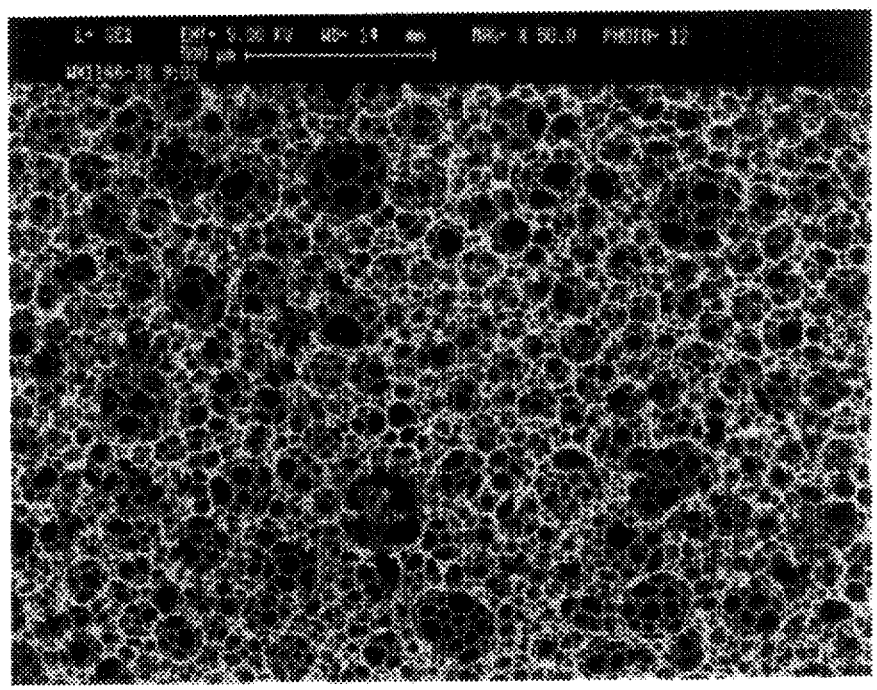
FIG. 3 of the drawings is a photomicrograph (50 X magnification) of a section of a representative absorbent polymeric foam according to the present invention made from HIPE having a 60:1 water-to-oil weight ratio and poured at 93° C., and where the monomer component consisted of a 21:14:55:10 weight ratio of ethyl styrene (EtS):divinyl benzene (DVB):2-ethylhexyl acrylate (EHA) :hexanediol diacrylate (HDDA) and where 5.5% (by weight of the oil phase) of diglycerol monooleate (DGMO) and 1% of ditallow dimethyl ammonium methylsulfate emulsifiers were used.
Figure 4:
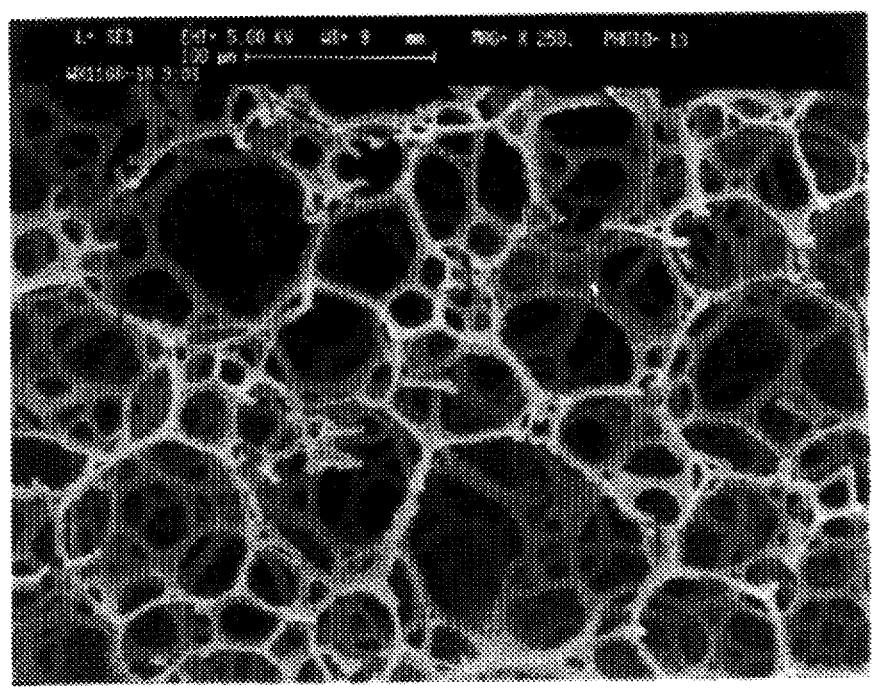
FIG. 4 of the drawings is a photomicrograph (250 X magnification) of the foam of FIG. 3.

Cell and hole sizes are parameters that can impact a number of important mechanical and performance features of the foams according to the present invention, including the fluid wicking properties of these foams, as well as the capillary pressure that is developed within the foam structure. A number of techniques are available for determining the average cell and hole sizes of foams. The most useful technique involves a simple measurement based on the scanning electron photomicrograph of a foam sample. FIGS. 3 and 4, for example, show a typical HIPE foam structure according to the present invention. Superimposed on the photomicrograph of FIG. 4 is a scale representing a dimension of 20 μm. Such a scale can be used to determine average cell and hole sizes by an image analysis procedure. The foams useful as absorbents for aqueous fluids in accordance with the present invention will preferably have a number average cell size of from about 20 to about 200 μm, and typically from about 30 to about 130 μm, and a number average hole size of from about 5 to about 30 μm, and typically from about 8 to about 25 μm.

Figure 5:
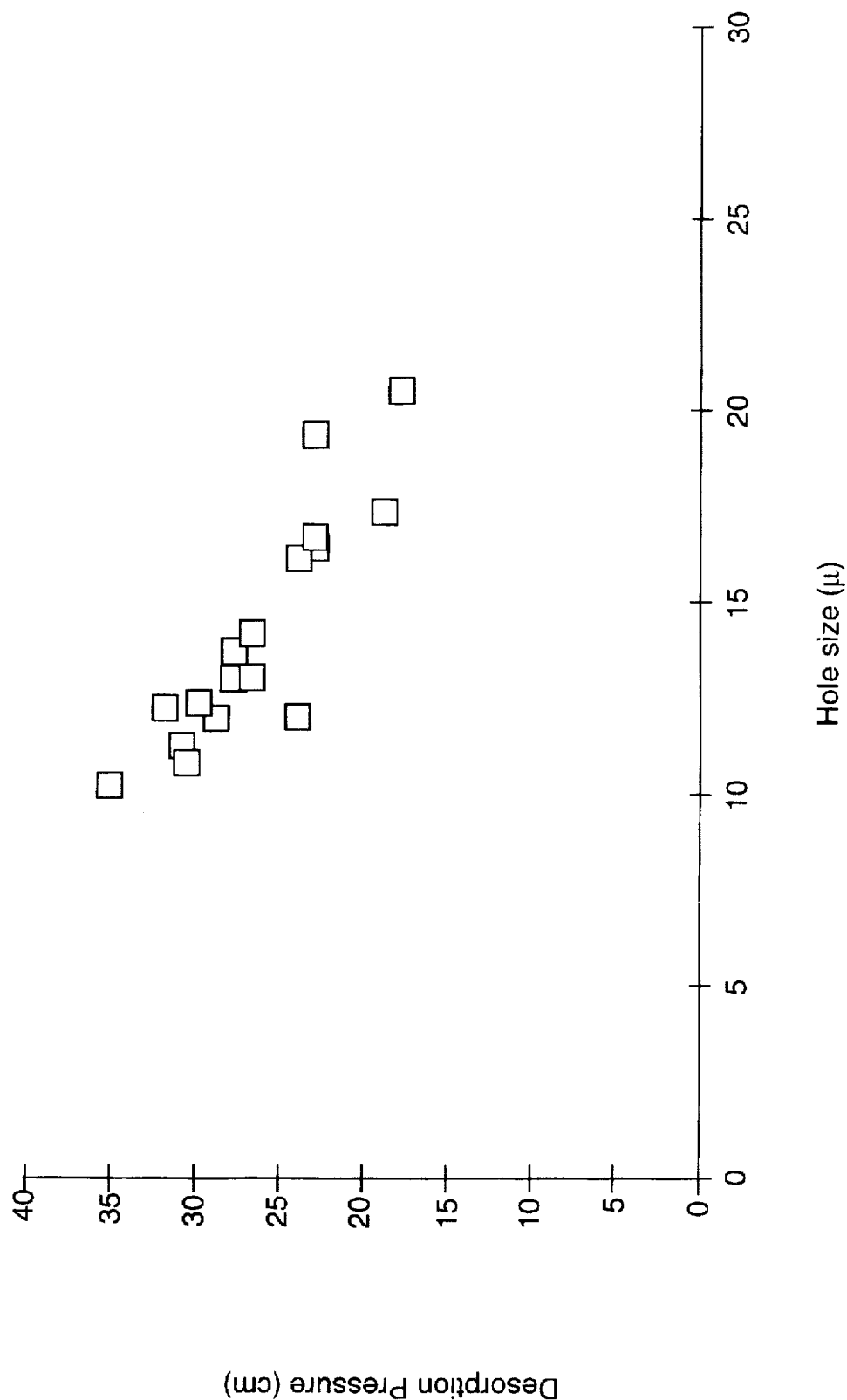
FIG. 5 of the drawings is a graphical plot showing fluid holding (desorption pressure) as a function of cell structure (hole size between cells) for several HIPE foams.

The relationship between the fluid holding ability and cell structure for these HIPE foams is shown in FIG. 5. FIG. 5 represents a plot of desorption pressures versus the number average hole size for a series of HIPE foams. As stated above, the desorption pressure of the foams of the present invention is one of the key factors that prevent these foams from collapsing when being desorbed or dewatered. The plot in FIG. 5 shows how one aspect of the foam structure (the hole size between cells) impacts this important feature. Indeed, as shown by this plot, as the number average hole size increases, the desorption pressure decreases in essentially a linear fashion.

2. Capillary Suction Specific Area

"Capillary suction specific surface area" is a measure of the test-liquid-accessible surface area of the polymeric network accessible to the test fluid. Capillary suction specific surface area is determined both by the dimensions of the cellular units in the foam and by the density of the polymer, and is thus a way of quantifying the total amount of solid surface provided by the foam network to the extent that such a surface participates in absorbency.

For purposes of this invention, capillary suction specific surface area is determined by measuring the amount of capillary uptake of a low surface tension liquid (e.g., ethanol) which occurs within a foam sample of a known mass and dimensions. A detailed description of such a procedure for determining foam specific surface area via the capillary suction method is set forth in the TEST METHODS section of copending U.S. patent application Ser. No 989,270 (Dyer et al.), filed Dec. 11, 1992, which is incorporated by reference. Any reasonable alternative method for determining capillary suction specific surface area can also be utilized.

The foams of the present invention useful as absorbents are those that have a capillary suction specific surface area of at least about 0.2 $m^2/g$. Typically, the capillary suction specific surface area is in the range from about 0.3 to about 4 $m^2/g$, preferably from about 0.3 to about 2.5 $m^2/g$, most preferably from about 0.3 to about 1.5 $m^2/g$.

3. Surface Area per Foam Volume

Specific surface area per foam volume can be useful for empirically defining foam structures that will not collapse, or remain in a collapsed state, when desorbed, e.g., dried or compressed while in a wet state. See copending U.S. application Ser. No. 989,270 (Dyer et al), filed Dec. 11, 1992 (herein incorporated by reference) where specific area per foam volume is discussed in detail with regard to collapsed foams. As used herein, "specific surface area per foam volume" refers to the capillary suction specific surface area of the foam structure times its foam density in the expanded state. It has been found that certain maximum specific surface area per foam volume values correlate with the ability of the foam structure to remain in an expanded state when desorbed, or to quickly return to an expanded state after being compressed while in a wet state. Foams according to the present invention have specific surface area per foam volume values of about 0.06 $m^2/cc$ or less, preferably from about 0.01 to about 0.04 $m^2/cc$, most preferably from about 0.01 to about 0.03 $m^2/cc$.

4. Foam Density

"Foam density" (i.e., in grams of foam per cubic centimeter of foam volume in air) is specified herein on a dry basis. The density of the foam, like capillary suction specific surface area, can influence a number of performance and mechanical characteristics of absorbent foams. These include the absorbent capacity for aqueous fluids and the compression deflection characteristics.

Any suitable gravimetric procedure that will provide a determination of mass of solid foam material per unit volume of foam structure can be used to measure foam density. For example, an ASTM gravimetric procedure described more fully in the TEST METHODS section of copending U.S. application Ser. No. 989,270 (Dyer et al), filed Dec. 11, 1992 (herein incorporated by reference) is one method that can be employed for density determination. Polymeric foams of the present invention useful as absorbents have dry basis density values in the range of from about 0.0079 to about 0.077 g/cc, preferably from about 0.011 to about 0.028 g/cc, and most preferably from about 0.013 to about 0.022 g/cc.

II. Preparation of Polymeric Foams from HIPE

A. In General

Polymeric foams according to the present invention can be prepared by polymerization of certain water-in-oil emulsions having a relatively high ratio of water phase to oil phase commonly known in the art as "HIPEs". Polymeric foam materials which result from the polymerization of such emulsions are referred to hereafter as "HIPE foams."

The relative amounts of the water and oil phases used to form the HIPEs are, among many other parameters, important in determining the structural, mechanical and performance properties of the resulting polymeric foams. In particular, the ratio of water to oil in the emulsion varies inversely with ultimate foam density and can influence the cell size and capillary suction specific surface area of the foam and dimensions of the struts that form the foam. The emulsions used to prepare the HIPE foams of this invention will generally have a volume to weight ratio of water phase to oil phase in the range of from about 12:1 to about 125:1, and most typically from about 35:1 to about 90:1. Particularly preferred foams can be made from HIPEs having ratios of from about 45:1 to about 75:1.

1. Oil Phase Components

The continuous oil phase of the HIPE comprises monomers that are polymerized to form the solid foam structure. This monomer component is formulated to be capable of forming a copolymer having a Tg of about 35° C. or lower, and typically from about 15° to about 30° C. (The method for determining Tg by Dynamic Mechanical Analysis (DMA) is described hereafter in the TEST METHODS section). This monomer component includes: (a) at least one monofunctional monomer whose atactic amorphous polymer has a Tg of about 25° C. or lower (see Brandup, J.; Immergut, E. H. "Polymer Handbook", 2nd Ed., Wiley-Interscience, New York, N.Y., 1975, M-139.); (b) at least one monofunctional comonomer to improve the toughness or tear resistance of the foam; (c) a first polyfunctional crosslinking agent; and (d) optionally a second polyfunctional crosslinking agent. Selection of particular types and amounts of monofunctional monomer(s) and comonomer(s) and polyfunctional cross-linking agent(s) can be important to the realization of absorbent HIPE foams having the desired combination of structure, mechanical, and fluid handling properties which render such materials suitable for use in the invention herein.

The monomer component comprises one or more monomers that tend to impart rubber-like properties to the resulting polymeric foam structure. Such monomers can produce high molecular weight (greater than 10,000) atactic amorphous polymers having Tg's of about 25° C. or lower. Monomers of this type include, for example, the ($C_4$–$C_{14}$) alkyl acrylates such as butyl acrylate, hexyl acrylate, octyl acrylate, 2-ethylhexyl acrylate, nonyl acrylate, decyl acrylate, dodecyl (lauryl) acrylate, isodecyl acrylate, tetradecyl acrylate, aryl acrylates and alkaryl acrylates such as benzyl acrylate, nonylphenyl acrylate, the ($C_6$–$C_{16}$) alkyl methacrylates such as hexyl methacrylate, octyl methacrylate, nonyl methacrylate, decyl methacrylate, isodecyl methacrylate, dodecyl (lauryl) methacrylate, tetradecyl methacrylate, ($C_4$–$C_{12}$) alkyl styrenes such as p-n-octylstyrene, acrylamides such as N-octadecyl acrylamide, isoprene, butadiene, and combinations of such monomers. Of these monomers, isodecyl acrylate, dodecyl acrylate and 2-ethylhexyl acrylate are the most preferred. The monofunctional monomer(s) will generally comprise 30 to about 80%, more preferably from about 50 to about 65%, by weight of the monomer component.

The monomer component utilized in the oil phase of the HIPEs also comprises one or more monofunctional comonomers capable of imparting toughness about equivalent to that provided by styrene to the resulting polymeric foam structure. Tougher foams exhibit the ability to deform substantially without failure. These monofunctional comonomer types can include styrene-based comonomers (e.g., styrene and ethyl styrene) or other monomer types such as methyl methacrylate where the related homopolymer is well known as exemplifying toughness. The preferred monofunctional comonomer of this type is a styrene-based monomer with styrene and ethyl styrene being the most preferred monomers of this kind. The monofunctional "toughening" comonomer will normally comprise from about 5 to about 40%, preferably from about 15% to about 25%, most preferably from about 18% about 24%, by weight of the monomer component.

In certain cases, the "toughening" comonomer can also impart the desired rubber-like properties to the resultant polymer. The $C_4$–$C_{12}$ alkyl styrenes, and in particular p-n-octylstyrene, are examples of such comonomers. For such comonomers, the amount of that can be included in the monomer component will be that of the typical monomer and comonomer combined.

The monomer component also contains a first (and optionally second) polyfunctional crosslinking agent. As with the monofunctional monomers and comonomers, selection of the particular type and amount of crosslinking agents is very important to the eventual realization of preferred polymeric foams having the desired combination of structural, mechanical, and fluid-handling properties.

The first polyfunctional crosslinking agent can be selected from a wide variety of monomers containing two or more activated vinyl groups, such as divinylbenzenes, trivinybenzenes, divinyltoluenes, divinylxylenes, divinylnaphthalenes divinylalkylbenzenes, divinylphenanthrenes, divinylbiphenyls, divinyldiphenylmethanes, divinylbenzyls, divinylphenylethers, divinyldiphenylsulfides, divinylfurans, divinylsulfide, divinyl sulfone, and mixtures thereof. Divinylbenzene is typically available as a mixture with ethyl styrene in proportions of about 55:45. These proportions can be modified so as to enrich the oil phase with one or the other component. Generally, it is advantageous to enrich the mixture with the ethyl styrene component while simultaneously reducing the amount of styrene in the monomer blend. The preferred ratio of divinylbenzene to ethyl styrene is from about 30:70 and 55:45, most preferably from about 35:65 to about 45:55. The inclusion of higher levels of ethyl styrene imparts the required toughness without increasing the Tg of the resulting copolymer to the degree that styrene does. This first cross-linking agent can generally be included in the oil phase of the HIPE in an amount of from about 5% to about 25%, more preferably from about 12% to about 20%, most preferably from about 12% to about 18%, by weight of the monomer component.

The optional second crosslinking agent can be selected from polyfunctional acrylates, methacrylates, acrylamides, methacrylamides, and mixtures thereof. These include di-, tri-, and tetra-acrylates, as well as di-, tri-, and tetra-methacrylates, di-, tri-, and tetra-acrylamides, as well as di-, tri-, and tetra- methacrylamides; and mixtures of these crosslinking agents. Suitable acrylate and methacrylate crosslinking agents can be derived from diols, triols and tetraols that include 1,10-decanediol, 1,8-octanediol, 1,6-hexanediol, 1,4-butanediol, 1,3-butanediol, 1,4-but-2-enediol, ethylene glycol, diethylene glycol, trimethylolpropane, pentaerythritol, hydroquinone, catechol, resorcinol triethylene glycol, polyethylene glycol, sorbitol, and the like. (The acrylamide and methacrylamide crosslinking agents can be derived from the equivalent diamines, triamines and tetramines). The preferred diols have at least 2, more preferably at least 4, most preferably 6, carbon atoms. This second crosslinking agent can generally be included in the oil phase of the HIPE in an amount of from 0 to about 15%, preferably from 0 to about 13%, by weight of the monomer component.

Without being bound by theory, it is believed this second crosslinking agent generates a more homogeneously crosslinked structure that develops strength more efficiently than using either the first or the second crosslinker alone at comparable levels. The second crosslinker also has the effect of broadening the glass-to-rubber transition region. This broader transition region can be tailored to meet specific strength and resilience requirements at in-use temperatures by controlling the relative amount of the two crosslinker types employed. Thus, a foam containing only the first type of crosslinker will exhibit a relatively narrow transition region. Increasing the amount of the second crosslinker serves to broaden the transition region, even if the actual transition temperature itself has not changed.

The major portion of the oil phase of the HIPEs will comprise the aforementioned monomers, comonomers and crosslinking agents. It is essential that these monomers, comonomers and crosslinking agents be substantially water-insoluble so that they are primarily soluble in the oil phase and not the water phase. Use of such substantially water-insoluble monomers ensures that HIPEs of appropriate characteristics and stability will be realized. It is, of course, highly preferred that the monomers, comonomers and crosslinking agents used herein be of the type such that the resulting polymeric foam is suitably non-toxic and appropriately chemically stable. These monomers, comonomers and cross-linking agents should preferably have little or no toxicity if present at very low residual concentrations during post-polymerization foam processing and/or use.

Another essential component of the oil phase is an emulsifier component that permits the formation of stable HIPEs. This emulsifier component comprises a primary emulsifier and optionally a secondary emulsifier. Suitable primary emulsifiers are those which: (1) are soluble in the oil phase of the HIPE; (2) provide a minimum oil phase/water phase interfacial tension (IFT) of from about 1 to about 10 dyne/cm, preferably about 2 to about 8 dyne/cm; (3) provide a critical aggregate concentration (CAC) of about 5 wt. % or less, preferably about 3 wt. % or less; (4) form HIPEs that are sufficiently stable against coalescence at the relevant drop sizes and the relevant process conditions (e.g., HIPE formation and polymerization temperatures); and (5) desirably have a high concentration of "interfacially active" component(s) capable of lowering the interfacial tension between the oil and water phases of the HIPE. While not being bound by theory, it is believed that the concentration of interfacially active components needs to be sufficiently high to provide at least approximately monolayer coverage to internal oil phase droplets at the preferred drop sizes, water:oil ratios, and emulsifier levels. It is also believed that a combination of a high minimum oil phase/water phase IFT and low CAC facilitates the formation of a stable HIPE having the suitably-large drop sizes for the formation of a foam having the preferred average cell and hole sizes of the present invention. Typically, these primary emulsifiers: (6) have melt and/or solid-to-liquid crystalline phase-transition temperatures of about 30° C. or less; (7) are water dispersible; and (8) are substantially water insoluble or at least do not appreciably partition into the water phase under the conditions of use. It is preferred that the primary emulsifier provide sufficient wettability when spread on a hydrophobic surface (e.g., the polymeric foam) such that the advancing contact angle for synthetic urine is less than (preferably substantially less than) 90°. The method of measurement for IFT and CAC is described in the TEST METHODS section hereafter.

Especially when used alone, these primary emulsifiers typically comprise at least about 40%, preferably at least about 50%, most preferably at least about 70%, emulsifying components selected from diglycerol monoesters of linear unsaturated $C_{16}-C_{22}$ fatty acids, diglycerol monoesters of branched $C_{16}-C_{24}$ fatty acids, diglycerol monoaliphatic ethers of branched $C_{16}-C_{24}$ alcohols, diglycerol monoaliphatic ethers of linear unsaturated $C_{16}-C_{22}$ alcohols, diglycerol monoaliphatic ethers of linear saturated $C_{12}-C_{14}$ alcohols, sorbitan monoesters of linear unsaturated $C_{16}-C_{22}$ fatty acids, sorbitan monoesters of branched $C_{16}-C_{24}$ fatty acids, and mixtures thereof. Preferred primary emulsifiers include diglycerol monooleate (e.g., preferably greater than about 40%, preferably greater than about 50%, most preferably greater than about 70% diglycerol monooleate) and sorbitan monooleate (e.g., preferably greater than about 40%, more preferably greater than about 50%, most preferably greater than about 70% sorbitan monooleate), and diglycerol monoisostearate (e.g., preferably greater than about 40%, more preferably greater than about 50%, most preferably greater than about 70% diglycerol monoisostearate).

Diglycerol monoesters of linear unsaturated and branched fatty acids useful as emulsifiers in the present invention can be prepared by esterifying diglycerol with fatty acids, using procedures well known in the art. See, for example, the method for preparing polyglycerol esters disclosed in copending U.S. application Ser. No. 989,270 (Dyer et al), filed Dec. 11, 1992, which is incorporated by reference. Diglycerol can be obtained commercially or can be separated from polyglycerols that are high in diglycerol. Linear unsaturated and branched fatty acids can be obtained commercially. The mixed ester product of the esterification reaction can be fractionally distilled under vacuum one or more times to yield distillation fractions that are high in diglycerol monoesters. For example, a A CMS-15A (C.V.C. Products Inc.; Rochester, N.Y.) continuous 14 inch centrifugal molecular still can be used for fractional distillation. Typically, the polyglycerol ester feedstock, while being heated, is first metered through a degasser unit and then to the heated evaporator cone of the still, where the vacuum distillation takes place. Distillate is collected on the bell jar surface, which can be heated to facilitate distillate removal. Distillate and residue are continuously removed by transfer pumps. The fatty acid composition of the resultant mixed ester product can be determined using high resolution gas chromatography. See copending U.S. application Ser. No. 989,270 (Dyer et al), filed Dec. 11, 1992, which is incorporated by reference. Polyglycerol and polyglycerol ester distribution of the resultant mixed ester product can be determined by capillary supercritical chromatography. See copending U.S. application Ser. No. 989,270 (Dyer et al), filed Dec. 11, 1992, which is incorporated by reference.

Linear saturated, linear unsaturated, or branched diglycerol monoaliphatic ethers can also be prepared and their composition determined using procedures well known in the art. See also copending U.S. application Ser. No. 08/514,346 (Stephen A. Goldman et al), filed Aug. 9, 1995, which is incorporated by reference.

Sorbitan monoesters of linear unsaturated and branched fatty acids can be obtained commercially or prepared using methods known in the art. See, for example, U.S. Pat. No. 4,103,047 (Zaki et al), issued Jul. 25, 1978 (herein incorporated by reference), especially column 4, line 32 to column 5, line 13. The mixed sorbitan ester product can be fractionally vacuum distilled to yield compositions that are high in sorbitan monoesters. Sorbitan ester compositions can be determined by methods well known in the art such as small molecule gel permeation chromatography. See copending U.S. application Ser. No. 08/514,346 (Stephen A. Goldman et al), filed Aug. 9, 1995, (herein incorporated by reference), which describes the use of this method for polyglycerol aliphatic ethers.

When these primary emulsifiers are used in combination with certain secondary emulsifiers, the primary emulsifier can comprise lower levels of these emulsifying components, i.e., as low as about 20% of these emulsifying components. These secondary emulsifiers are at least cosoluble with the primary emulsifier in the oil phase and can be included to:

(1) increase the stability of the HIPE against coalescence of the dispersed water droplets, especially at higher water-to-oil ratios and higher HIPE formation and polymerization temperatures, (2) raise the minimum oil phase/water phase IFT, (3) lower the CAC of the emulsifier component, or (4) increase the concentration of interfacially active components. While not being bound by theory, it is believed that the ability of the secondary emulsifier to maintain a high oil phase/water phase IFT and low CAC for the emulsifier component extends the range of HIPE formation and pour temperatures (e.g., to about 50° C. or higher) over which a stable high water:oil ratio HIPE can be made that has the large drop sizes suitable for the formation of polymeric foams having the preferred average cell and hole sizes of the present invention. Suitable secondary emulsifiers can be cationic types, including the long chain $C_{12}$–$C_{22}$ dialiphatic, short chain $C_1$–$C_4$ dialiphatic quaternary ammonium salts such as ditallow dimethyl ammonium chloride, bistridecyl dimethyl ammonium chloride, and ditallow dimethyl ammonium methylsulfate, the long chain $C_{12}$–$C_{22}$ dialkoyl (alkenoyl)-2-hydroxyethyl, short chain $C_1$–$C_4$ dialiphatic quaternary ammonium salts such as ditallowoyl-2-hydroxyethyl dimethyl ammonium chloride, the long chain $C_{12}$–$C_{22}$ dialiphatic imidazolinium quaternary ammonium salts such as methyl-1-tallow amido ethyl-2-tallow imidazolinium methylsulfate and methyl-1-oleyl amido ethyl-2-oleyl imidazolinium methylsulfate, the short chain $C_1$–$C_4$ dialiphatic, the long chain $C_{12}$–$C_{22}$ monoaliphatic benzyl quaternary ammonium salts such as dimethyl stearyl benzyl ammonium chloride; anionic types including the $C_6$–$C_{18}$ dialiphatic esters of sodium sulfosuccinic acid such as the dioctyl ester of sodium sulfosuccinic acid and the bistridecyl ester of sodium sulfosuccinic acid; and mixtures of these secondary emulsifiers. These secondary emulsifiers can be obtained commercially or prepared using methods known in the art. The preferred secondary emulsifiers are ditallow dimethyl ammonium methyl sulfate and ditallow dimethyl ammonium methyl chloride. When these optional secondary emulsifiers are included in the emulsifier component, it is in a weight ratio of primary to secondary emulsifier of from about 50:1 to about 1:4, preferably from about 30:1 to about 2:1.

The oil phase used to form the HIPEs comprises from about 85 to about 98% by weight monomer component and from about 2 to about 15% by weight emulsifier component. Preferably, the oil phase will comprise from about 90 to about 97% by weight monomer component and from about 3 to about 10% by weight emulsifier component. The oil phase also can contain other optional components. One such optional component is an oil soluble polymerization initiator of the general type well known to those skilled in the art, such as described in U.S. Pat. No. 5,290,820 (Bass et al), issued Mar. 1, 1994, which is incorporated by reference. Another preferred optional component is an antioxidant such as a Hindered Amine Light Stabilizer (HALS) and Hindered Phenolic Stabilizers (HPS) or any other antioxidant compatible with the initiator system to be employed. Other optional components include plasticizers, fillers, colorants, chain transfer agents, dissolved polymers, and the like.

2. Water Phase Components

The discontinuous water internal phase of the HIPE is generally an aqueous solution containing one or more dissolved components. One essential dissolved component of the water phase is a water-soluble electrolyte. The dissolved electrolyte minimizes the tendency of the monomers, comonomers and crosslinkers that are primarily oil soluble to also dissolve in the water phase. This, in turn, is believed to minimize the extent to which polymeric material fills the cell windows at the oil/water interfaces formed by the water phase droplets during polymerization. Thus, the presence of electrolyte and the resulting ionic strength of the water phase is believed to determine whether and to what degree the resulting preferred polymeric foams can be open-celled.

Any electrolyte capable of imparting ionic strength to the water phase can be used. Preferred electrolytes are mono-, di-, or trivalent inorganic salts such as the water-soluble halides, e.g., chlorides, nitrates and sulfates of alkali metals and alkaline earth metals. Examples include sodium chloride, calcium chloride, sodium sulfate and magnesium sulfate. Calcium chloride is the most preferred for use in the present invention. Generally the electrolyte will be utilized in the water phase of the HIPEs in a concentration in the range of from about 0.2 to about 20% by weight of the water phase. More preferably, the electrolyte will comprise from about 1 to about 10% by weight of the water phase.

The HIPEs will also typically contain a polymerization initiator. Such an initiator component is generally added to the water phase of the HIPEs and can be any conventional water-soluble free radical initiator. These include peroxygen compounds such as sodium, potassium and ammonium persulfates, hydrogen peroxide, sodium peracetate, sodium percarbonate and the like. Conventional redox initiator systems can also be used. Such systems are formed by combining the foregoing peroxygen compounds with reducing agents such as sodium bisulfite, L-ascorbic acid or ferrous salts.

The initiator can be present at up to about 20 mole percent based on the total moles of polymerizable monomers present in the oil phase. More preferably, the initiator is present in an amount of from about 0.001 to about 10 mole percent based on the total moles of polymerizable monomers in the oil phase.

3. Hydrophilizing Surfactants and Hydratable Salts

The polymer forming the HIPE foam structure will preferably be substantially free of polar functional groups. This means the polymeric foam will be relatively hydrophobic in character. These hydrophobic foams can find utility where the absorption of hydrophobic fluids is desired. Uses of this sort include those where an oily component is mixed with water and it is desired to separate and isolate the oily component, such as in the case of marine oil spills.

When these foams are to be used as absorbents for aqueous fluids such as juice spills, milk and the like for clean up and/or bodily fluids such as urine, they generally require further treatment to render the foam relatively more hydrophilic. Hydrophilization of the foam, if necessary, can generally be accomplished by treating the HIPE foam with a hydrophilizing surfactant in a manner described more fully hereafter.

These hydrophilizing surfactants can be any material that enhances the water wettability of the polymeric foam surface. They are well known in the art, and can include a variety of surfactants, preferably of the nonionic type. They will generally be liquid form, and can be dissolved or dispersed in a hydrophilizing solution that is applied to the HIPE foam surface. In this manner, hydrophilizing surfactants can be adsorbed by the preferred HIPE foams in amounts suitable for rendering the surfaces thereof substantially hydrophilic, but without substantially impairing the desired flexibility and compression deflection characteristics of the foam. Such surfactants can include all of those previously described for use as the oil phase emulsifier for the HIPE, such as diglycerol monooleate, sorbitan monooleate and diglycerol monoisostearate. In preferred foams, the hydrophilizing surfactant is incorporated such that residual amounts of the agent that remain in the foam structure are in the range from about 0.5% to about 15%, preferably from about 0.5 to about 6%, by weight of the foam.

Another material that is typically incorporated into the HIPE foam structure is a hydratable, and preferably hygroscopic or deliquescent, water soluble inorganic salt. Such salts include, for example, toxicologically acceptable alkaline earth metal salts. Salts of this type and their use with oil-soluble surfactants as the foam hydrophilizing surfactant is described in greater detail in U.S. Pat. No. 5,352,711 (DesMarais), issued Oct. 4, 1994, the disclosure of which is incorporated by reference. Preferred salts of this type include the calcium halides such as calcium chloride that, as previously noted, can also be employed as the water phase electrolyte in the HIPE.

Hydratable inorganic salts can easily be incorporated by treating the foams with aqueous solutions of such salts. These salt solutions can generally be used to treat the foams after completion of, or as part of, the process of removing the residual water phase from the just-polymerized foams. Treatment of foams with such solutions preferably deposits hydratable inorganic salts such as calcium chloride in residual amounts of at least about 0.1% by weight of the foam, and typically in the range of from about 0.1 to about 12%.

Treatment of these relatively hydrophobic foams with hydrophilizing surfactants (with or without hydratable salts) will typically be carried out to the extent necessary to impart suitable hydrophilicity to the foam. Some foams of the preferred HIPE type, however, are suitably hydrophilic as prepared, and can have incorporated therein sufficient amounts of hydratable salts, thus requiring no additional treatment with hydrophilizing surfactants or hydratable salts. In particular, such preferred HIPE foams include those where certain oil phase emulsifiers previously described and calcium chloride are used in the HIPE. In those instances, the internal polymerized foam surfaces will be suitably hydrophilic, and will include residual water-phase liquid containing or depositing sufficient amounts of calcium chloride, even after the polymeric foams have been dewatered to a practicable extent.

B. Processing Conditions for Obtaining HIPE Foams

Foam preparation typically involves the steps of: 1) forming a stable high internal phase emulsion (HIPE); 2) polymerizing/curing this stable emulsion under conditions suitable for forming a solid polymeric foam structure; 3) optionally washing the solid polymeric foam structure to remove the original residual water phase from the polymeric foam structure and, if necessary, treating the polymeric foam structure with a hydrophilizing surfactant and/or hydratable salt to deposit any needed hydrophilizing surfactant/ hydratable salt, and 4) thereafter dewatering this polymeric foam structure.

1. Formation of HIPE

The HIPE is formed by combining the oil and water phase components in the previously specified weight ratios. The oil phase will typically contain the requisite monomers, comonomers, crosslinkers, and emulsifiers, as well as optional components such as plasticizers, antioxidants, flame retardants, and chain transfer agents. The water phase will typically contain electrolytes and polymerization initiators, as well as optional components such as water-soluble emulsifiers.

The HIPE can be formed from the combined oil and water phases by subjecting these combined phases to shear agitation. Shear agitation is generally applied to the extent and for a time period necessary to form a stable emulsion. Such a process can be conducted in either batchwise or continuous fashion and is generally carried out under conditions suitable for forming an emulsion where the water phase droplets are dispersed to such an extent that the resulting polymeric foam will have the requisite cell size and other structural characteristics. Suitable mixing or agitation devices are those that are capable of forming an emulsion under conditions of low shear mixing. Emulsification of the oil and water phase combination will frequently involve the use of a mixing or agitation device such as a pin impeller.

One preferred method of forming such HIPEs involves a continuous process that combines and emulsifies the requisite oil and water phases. In such a process, a liquid stream comprising the oil phase is formed. Concurrently, a liquid stream comprising the water phase is also formed. The two streams are then combined in a suitable mixing chamber or zone such that the requisite water to oil phase weight ratios previously specified are achieved.

In the mixing chamber or zone, the combined streams are generally subjected to low shear agitation provided, for example, by a pin impeller of suitable configuration and dimensions. Shear will typically be applied to the combined oil/water phase stream at a rate of about 4000 sec$^{-1}$ or less, preferably about 3000 sec$^{-1}$ or less. Once formed, the stable liquid HIPE can then be withdrawn from the mixing chamber or zone. This preferred method for forming HIPEs via a continuous process is described in greater detail in U.S. Pat. No. 5,149,720 (DesMarais et. al), issued Sep. 22, 1992, which is incorporated by reference. See also copending U.S. application Ser. No. 08/716,510 (Thomas A. DesMarais), filed Sep. 17, 1996, Case No. 5543 (herein incorporated by reference), which describes an improved continuous process having a recirculation loop for the HIPE.

One particular advantage of the more robust emulsifier systems used in these HIPEs is that the mixing conditions during HIPE formation and pouring can be carried out at more elevated temperatures of about 50° C. or higher, preferably 60° C. or higher. Typically, the HIPE can be formed at a temperature of from about 60° C. to about 99° C., more typically from about 65° to about 95° C.

2. Polymerization/Curing of the HIPE

The HIPE formed will generally be collected or poured into a suitable reaction vessel, container or region to be polymerized or cured. In one embodiment, the reaction vessel comprises a tub constructed of polyethylene from which the eventually polymerized/cured solid foam material can be easily removed for further processing after polymerization/curing has been carried out to the extent desired. It is usually preferred that the temperature at which the HIPE is poured into the vessel be approximately the same as the polymerization/curing temperature.

Suitable polymerization/curing conditions will vary depending upon the monomer and other makeup of the oil and water phases of the emulsion (especially the emulsifier systems used), and the type and amounts of polymerization initiators used. Frequently, however, suitable polymerization/curing conditions will involve maintaining the HIPE at elevated temperatures above about 50° C., more preferably above about 65° C., and most preferably above about 80° C., for a time period ranging from about 2 to about 64 hours, more preferably from about 2 to about 48 hours. An advantage of the more robust emulsifier systems used is that coalescence is minimized when polymerization/curing is carried out at higher temperatures. The HIPE can also be cured in stages such as described in U.S. Pat. No. 5,189,070

(Brownscombe et al), issued Feb. 23, 1993, which is herein incorporated by reference.

A porous water-filled open-celled HIPE foam is typically obtained after polymerization/curing in a reaction vessel, such as a tub. This polymerized HIPE foam is typically cut or sliced into a sheet-like form. Sheets of polymerized HIPE foam are easier to process during subsequent treating/washing and dewatering steps, as well as to prepare the HIPE foam for use in absorbent articles. The polymerized HIPE foam is typically cut/sliced to provide a cut thickness in the range of from about 0.08 to about 2.5 cm.

3. Treating/Washing HIPE Foam

The solid polymerized HIPE foam formed will generally be filled with residual water phase material used to prepare the HIPE. This residual water phase material (generally an aqueous solution of electrolyte, residual emulsifier, and polymerization initiator) should be at least partially removed prior to further processing and use of the foam. Removal of this original water phase material will usually be carried out by compressing the foam structure to squeeze out residual liquid and/or by washing the foam structure with water or other aqueous washing solutions. Frequently several compressing and washing steps, e.g., from 2 to 4 cycles, will be used.

After the original water phase material has been removed to the extent required, the HIPE foam, if needed, can be treated, e.g., by continued washing, with an aqueous solution of a suitable hydrophilizing surfactant and/or hydratable salt. Hydrophilizing surfactants and hydratable salts that can be employed have been previously described. As noted, treatment of the HIPE foam with the hydrophilizing surfactant/hydratable salt solution continues, if necessary, until the desired amount of hydrophilizing surfactant/hydratable salt has been incorporated and until the foam exhibits the desired adhesion tension value for any test liquid of choice.

For certain absorbent uses, removal of most of the residual electrolyte (i.e., hydratable salts) from the foam can be desirable. For example, removal of these salts is particularly important when the foam is to be used in an absorbent core (as described hereafter) that also has a fluid storage component that contains absorbent gelling materials. In these circumstances, the level of these residual hydratable salts in the foam is reduced as much as possible during this washing step, typically to about 2% or less, preferably to about 0.5% or less. After the removal of these salts, the HIPE foam will typically require treatment with an effective amount of a suitable hydrophilizing surfactant to rehydrophilize the foam.

4. Foam Dewatering

After the HIPE foam has been treated/washed, it will generally be dewatered. Dewatering can be achieved by compressing the foam (preferably in the z-direction) to squeeze out residual water, by subjecting the foam and the water therein to temperatures of from about 60° to about 200° C., or to microwave treatment, by vacuum dewatering or by a combination of compression and thermal drying/microwave/vacuum dewatering techniques. The dewatering step will generally be carried out until the HIPE foam is ready for use and is as dry as practicable. Frequently such compression dewatered foams will have a water (moisture) content of from about 50 to about 500%, more preferably from about 50 to about 200%, by weight on a dry weight basis. Subsequently, the compressed foams can be thermally dried to a moisture content of from about 5 to about 40%, more preferably from about 5 to about 15%, on a dry weight basis.

III. Uses of Polymeric Foams

A. In General

Polymeric foams according to the present invention are broadly useful in absorbent cores of disposable diapers, as well as other absorbent articles. These foams can also be employed as environmental waste oil sorbents; as absorbent components in bandages or dressings; to apply paint to various surfaces; in dust mop heads; in wet mop heads; in dispensers of fluids; in packaging; in shoes as odor/moisture sorbents; in cushions; in gloves, and for many other uses.

B. Absorbent Articles

Absorbent foams of the present invention are particularly useful as at least a portion of the absorbent structures (e.g., absorbent cores) for various absorbent articles. By "absorbent article" herein is meant a consumer product that is capable of absorbing significant quantities of urine, or other fluids like aqueous fecal matter (runny bowel movements), discharged by an incontinent wearer or user of the article. Examples of such absorbent articles include disposable diapers, incontinence garments, catamenials such as tampons and sanitary napkins, disposable training pants, bed pads, and the like. The absorbent foam structures herein are particularly suitable for use in articles such as diapers, sanitary napkins, tampons, incontinence pads or garments, clothing shields, and the like.

The absorbent foams of the present invention provide good aesthetics due to their soft, resilient structure and physical integrity. In sheet form, these absorbent foams can also be relatively easy to configure for use in a variety of absorbent articles. In contrast to fibrous absorbent components, these absorbent foams remain largely unchanged in overall appearance and structure during use, i.e. density, shape, thickness, etc. Since these absorbent foams are not plasticized by aqueous fluids, their mechanical properties remain largely unchanged when wet.

Because the foams of the present invention rapidly acquire and distribute aqueous fluids, they are, particularly useful as the fluid acquisition/distribution component of an absorbent core. These acquisition/distribution foams combine relatively high capillary absorption pressures and capacity-per-weight properties that allows them to acquire fluid with or without the aid of gravity, therefore keeping the wearer's skin dry. This high capacity (per given weight) can lead to light-weight, efficient products.

In addition, because the absorbent foams of the present invention can give up this acquired fluid efficiently to other absorbent components, these foams are particularly useful as the upper acquisition/distribution component in a "multi-layer" absorbent core that additionally contains a lower fluid storage/redistribution component, where the absorbent core is positioned between the topsheet and backsheet to form the absorbent article. For purposes of the present invention, an "upper" layer of a multi-layer absorbent core is a layer that is relatively closer to the body of the wearer, e.g., the layer closest to the article topsheet. The term "lower" layer conversely means a layer of a multi-layer absorbent core that is relatively further away from the body of the wearer, e.g., the layer closest to the article backsheet. This lower fluid storage/redistribution layer is typically positioned within the absorbent core so as to underlie the (upper) fluid acquisition/distribution layer and be in fluid communication therewith. This lower storage/redistribution layer can comprise a variety of fluid storage/redistribution components including those containing absorbent gelling materials such as disclosed in U.S. Pat. No. 5,061,259 (Goldman et al), issued Oct. 29, 1991, U.S. Pat. No. 4,654,039 (Brandt et al), issued Mar. 31, 1987 (reissued Apr. 19, 1988 as Re. 32,649), U.S.

Pat. No. 4,666,983 (Tsubakimoto et al), issued May 19, 1987, and U.S. Pat. No. 4,625,001 (Tsubakimoto et al), issued Nov. 25, 1986, all of which are incorporated by reference; absorbent macrostructures made from these absorbent gelling materials such as those disclosed in U.S. Pat. No. 5,102,597 (Roe et al), issued Apr. 7, 1992, and U.S. Pat. No. 5,324,561 (Rezai et al), issued Jun. 23, 1994, both of which are incorporated by reference); absorbent gelling materials laminated between two tissue layers such as those disclosed in U.S. Pat. No. 4,260,443 (Lindsay et al), issued Apr. 7, 1981, U.S. Pat. No. 4,467,012 (Pedersen et al), issued Aug. 21, 1984, U.S. Pat. No. 4,715,918 (Lang), issued Dec. 29, 1987, U.S. Pat. No. 4,851,069 (Packard et al), issued Jul. 25, 1989, U.S. Pat. No. 4,950,264 (Osborn), issued Aug. 21, 1990; U.S. Pat. No. 4,994,037 (Bernardin), issued Feb. 19, 1991; U.S. Pat. No. 5,009,650 (Bernardin), issued Apr. 23, 1991; U.S. Pat. No. 5,009,653 (Osborn), issued Apr. 23, 1991; U.S. Pat. No. 5,128,082 (Makoui), Jul. 7, 1992; U.S. Pat. No. 5,149,335 (Kellenberger et al), issued Sep. 22, 1992; and U.S. Pat. No. 5,176,668 (Bernardin), issued Jan. 5, 1993, all of which are incorporated by reference; and absorbent foams capable of storing acquired fluids such as those disclosed in U.S. Pat. No. 5,268,224 (DesMarais et al.), issued Dec. 7, 1993, copending U.S. application Ser. No. 989,270 (Dyer et al), filed Dec. 11, 1992, and copending U.S. application Ser. No. 08/563,866 (Thomas A. DesMarais et al), filed Nov. 29, 1995, all of which are incorporated by reference.

There is no particular criticality with respect to the positional relationship of the fluid acquisition/distribution foam component and the fluid storage/redistribution component within these multi-layer absorbent cores so long as these components are in effective fluid communication with each other and so long as each component is large enough to effectively hold and/or transport the amount of aqueous body fluid that is expected to be discharged into the absorbent article. One suitable relationship between the fluid acquisition/distribution foam component and the fluid storage/redistribution component within the absorbent core is to place these components in a layered configuration. In such a layered configuration, the fluid acquisition/distribution foam component comprises an upper foam layer which overlies a subjacent fluid storage/redistribution component in the form of a lower layer. It should be understood that these two types of layers refer merely to the upper and lower zones of the absorbent core and are not necessarily limited to single layers or sheets. Both the fluid acquisition/distribution zone, e.g., upper layer, and the fluid storage/redistribution zone, e.g., lower layer, can comprise several layers of the requisite type. Thus, as used herein, the term "layer" includes the terms "layers" and "layered."

The absorbent articles typically comprise a fluid impervious backsheet, a fluid pervious topsheet joined to, or otherwise associated with the backsheet, and an absorbent core according to the present invention positioned between the backsheet and the topsheet. The topsheet is positioned adjacent the body surface of the absorbent core. The topsheet is preferably joined to the backsheet by attachment means such as those well known in the art. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In preferred absorbent articles, the topsheet and the backsheet are joined directly to each other at the periphery thereof.

The backsheet is typically impervious to body fluids and is preferably manufactured from a thin plastic film, although other flexible fluid impervious materials may also be used. As used herein, the term "flexible" refers to materials that are compliant and will readily conform to the general shape and contours of the human body. The backsheet prevents body fluids absorbed and contained in the absorbent core from wetting clothes that contact the articles such as pants, pajamas, undergarments, and the like. The backsheet can comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet can permit vapors to escape from the absorbent core (i.e., breathable) while still preventing body fluids from passing through the backsheet.

The topsheet is compliant, soft feeling, and non-irritating to the wearer's skin. Further, the topsheet is fluid pervious permitting body fluids to readily penetrate through its thickness. A suitable topsheet can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

Preferred topsheets for use in absorbent articles of the present invention are selected from high loft nonwoven topsheets and apertured formed film topsheets. Apertured formed films are especially preferred for the topsheet because they are pervious to body fluids and yet non-absorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135 (Thompson), issued Dec. 30, 1975; U.S. Pat. No. 4,324,246 (Mullane, et al.), issued Apr. 13, 1982; U.S. Pat. No. 4,342,314 (Radel. et al.), issued Aug. 3, 1982; U.S. Pat. No. 4,463,045 (Ahr et al.), issued Jul. 31, 1984; and U.S. Pat. No. 5,006,394 (Baird), issued Apr. 9, 1991. Each of these patents are incorporated herein by reference. Suitable microapertured formed film topsheets are disclosed in U.S. Pat. No. 4,609,518 (Curro et al), issue Sep. 2, 1986 and U.S. Pat. No. 4,629,643 (Curro et al), issued Dec. 16, 1986, which are incorporated by reference.

The body surface of the formed film topsheet can be hydrophilic so as to help body fluids to transfer through the topsheet faster than if the body surface was not hydrophilic so as to diminish the likelihood that fluid will flow off the topsheet rather than flowing into and being absorbed by the absorbent structure. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated by reference. Alternatively, the body surface of the topsheet can be made hydrophilic by treating it with a surfactant such as is described in the above referenced U.S. Pat. No. 4,950,254, incorporated herein by reference.

In some embodiments according to the present invention, the acquisition/distribution layer of the absorbent core will be placed in a specific positional relationship with respect to the topsheet and the storage/redistribution layer of the absorbent core. More particularly, the acquisition/ distribution layer of the core is positioned so that it is effectively located to acquire discharged body fluid and transport such fluid to other regions of the core. Thus the acquisition/distribution layer can encompass the vicinity of the point of discharge of body fluids. These areas would include the crotch area and, preferably for articles to be worn by males, also the region where urination discharges occur in the front of the diaper. For a diaper, the front of the absorbent articles means the portion of the absorbent article which is intended to be placed on the front of the wearer. Additionally, for male wearers, it is desirable for the acquisition/distribution layer to extend to near the front waist area of the wearer to effectively acquire the relatively high fluid load that occurs in the front of diapers for male wearers, and to compensate for directional variations of the discharges. The corresponding absorbent article regions can vary depending upon the design and fit of the absorbent article.

For diaper executions, the acquisition/distribution layer of the core can be positioned relative to an elongated topsheet and/or the storage/redistribution layer such that the acquisition/distribution layer is of sufficient length to extend to areas corresponding at least to about 50%, preferably 75%, of the length of the topsheet and/or from about 50 to about 120% of the length of the storage/redistribution layer. The acquisition/distribution foam layer should have a width sufficient to acquire gushes of body fluids and to prevent direct discharge of fluid onto the storage/redistribution layer. Generally, for diapers, the width of the acquisition/ distribution layer will be at least about 5 cm, preferably at least about 6 cm.

For purposes of determining such acquisition/distribution foam layer positioning, the length of the absorbent article will be taken as the normal longest longitudinal dimension of the elongated article backing sheet. This normal longest dimension of the elongated backing sheet can be defined with respect to the article as it is applied to the wearer. When worn, the opposing ends of the back sheet are fastened together so that these joined ends form a circle around the wearer's waist. The normal length of the backing sheet will thus be the length of the line running through the back sheet from a) the point on the edge of the back sheet at the middle of the wearer's back waist, through the crotch, to b) the point on the opposite edge of the backing sheet at the middle of the wearer's front waist. The size and shape of the topsheet will generally correspond substantially to the back sheet.

In the usual instance, the storage/redistribution layer of the absorbent cores which generally defines the shape of the absorbent article and the normal length of the elongated article topsheet will be approached by the longest longitudinal dimension of the storage/redistribution layer of the core. However, in some articles (e.g., adult incontinence articles) where bulk reduction or minimum cost are important, the storage/redistribution layer would be generally located to cover only the genital region of the wearer and a reasonable area proximate to the genital area. In this instance both the fluid acquisition/distribution layer and the storage/redistribution layer would be located toward the front of the article as defined by the topsheet such that the acquisition/distribution and storage/redistribution layers would typically be found in the front two-thirds of the article length.

The acquisition/distribution foam layer can be of any desired shape consistent with comfortable fit and the sizing limitations discussed above. These shapes include, for example, circular, rectangular, trapezoidal or oblong, e.g., hourglass-shaped, dog-bone-shaped, half dog bone shaped, oval or irregularly shaped. The acquisition/distribution foam layer can be of similar shape or differing shape than the storage/redistribution layer. The storage/redistribution layer of the preferred absorbent core configuration can also be of any desired shape consistent with comfortable fit including, for example, circular, rectangular, trapezoidal or oblong, e.g., hourglass-shaped, dog-bone-shaped, half dog bone shaped, oval or irregularly shaped. The storage/ redistribution layer need not be physically separated from the acquisition/distribution layer or completely unattached from the storage/redistribution layer.

Figures 6, 7:
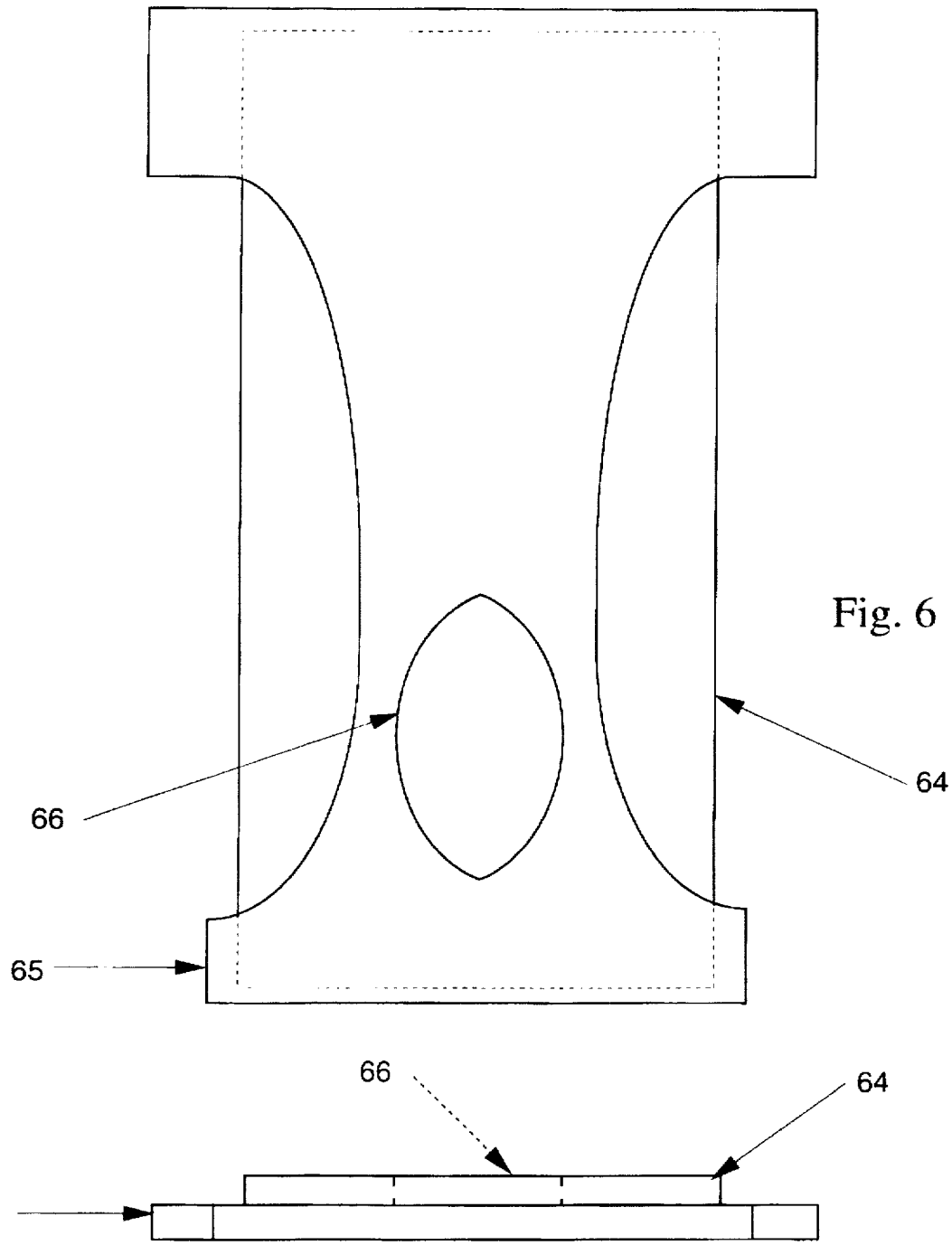
FIGS. 6 and 7 of the drawings represent, respectively, a top view and a side view of a multi-layer core configuration where the fluid storage/redistribution component overlies a subjacent fluid acquisition/distribution component.

FIGS. 6 and 7 show a multi-layer absorbent core configuration where the fluid storage/redistribution component comprises a generally rectangularly-shaped top layer 64 which is placed over an underlying hourglass-shaped fluid acquisition/distribution lower foam layer 65. The fluid storage/redistribution layer contains a fluid acquisition aperture 66 through which body fluid is discharged so as to impinge on the subjacent acquisition/distribution lower layer 65.

Figure 8:
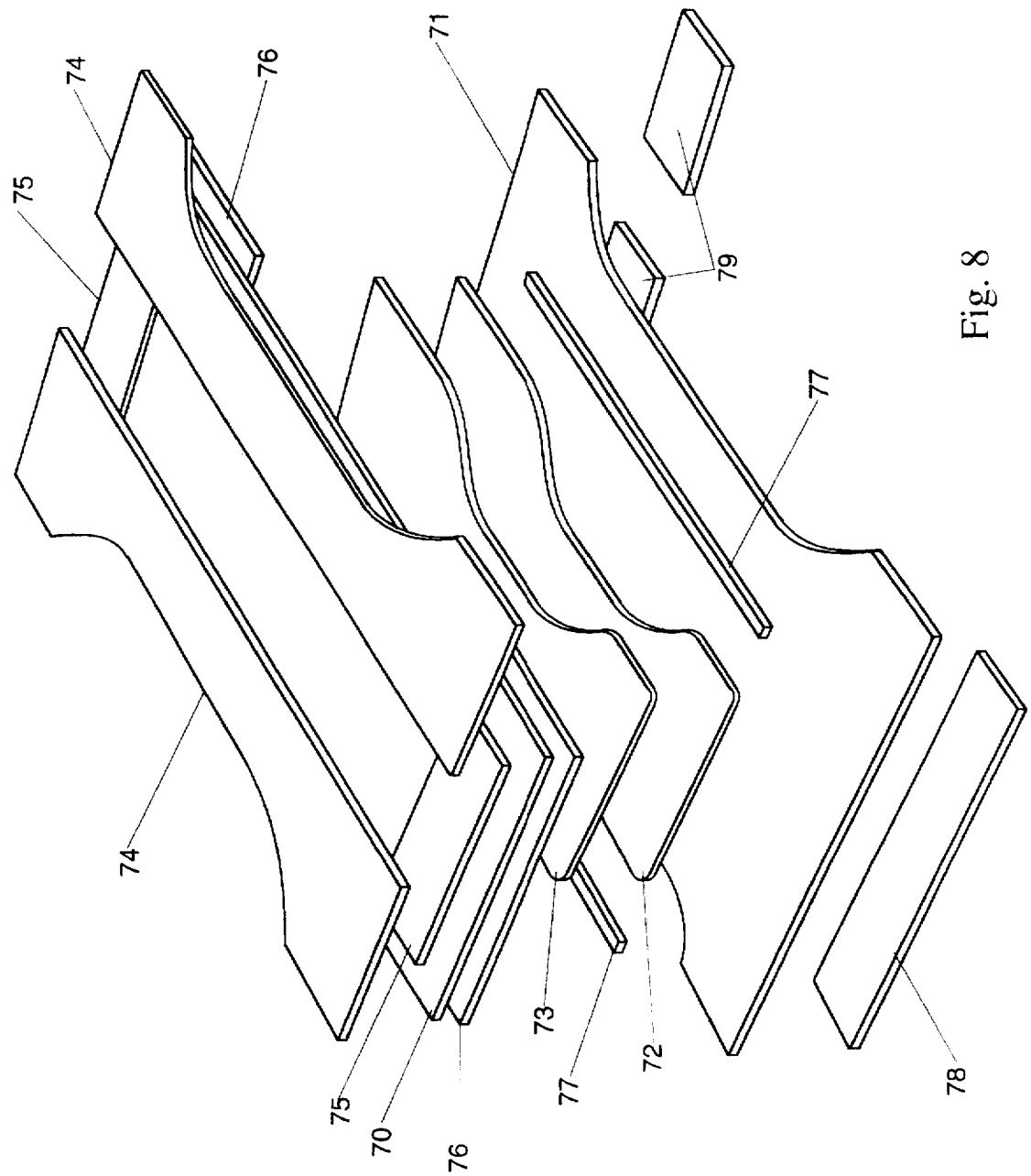
FIG. 8 of the drawings represents a blown-apart view of the components of a diaper structure also of multi-layer core configuration having an hourglass-shaped fluid acquisition/ distribution foam layer overlying a fluid storage/ redistribution layer with a modified hourglass shape.

FIG. 8 shows a disposable diaper having another multi-layer absorbent core configuration. Such a diaper comprises a topsheet, 70, a fluid-impervious backsheet, 71, and a dual layer absorbent core positioned between the topsheet and the backsheet. The dual layer absorbent core comprises a modified hourglass-shaped, fluid storage/redistribution layer 72 positioned below a modified-hourglass shaped fluid acquisition/distribution foam layer, 73. The topsheet contains two substantially parallel barrier leg cuff strips 74 with elastic. Affixed to the diaper backsheet are two rectangular elasticized waistband members 75. Also affixed to each end of the backsheet are two waistshield elements 76. Also affixed to the backsheet are two parallel leg elastic strips 77. A sheet 78 is affixed to the outside of the backsheet as a dedicated fastening surface for two pieces 79 of Y-tape which can be used to fasten the diaper around the wearer.

Multi-layer absorbent cores can also be made according to copending U.S. application Ser. No. b 08/521,556(Gary Dean LaVon et al), filed Aug. 30, 1995, (herein incorporated by reference), where one or more layers comprise an absorbent foam according to the present invention.

IV. Test Methods

A. Capillary Absorption Pressure

A capillary absorption isotherm curve is generated using the Vertical Wicking Absorbent Capacity test described in the TEST METHODS section of copending U.S. application Ser. No. 989,270 (Dyer et al), filed Dec. 11, 1992, which is incorporated by reference, except at 31° C. rather than 37° C. The curve is a plot of the absorbent capacity of each segment as a function of wicked height, using the distance from the top of the water reservoir to the midpoint of each segment for the height h. The capillary absorption pressure is taken as the height of the foam that has an absorbent capacity one-half of the foam's free absorbent capacity.

B. Capillary Desorption Pressure

Capillary desorption pressure is a measure of the foam's ability to hold onto fluid as a function of various hydrostatic heads. The sample strip of suitable dimensions, e.g., 40 cm long×2.5 cm wide×0.2 cm thick, and the test liquid (distilled water, optionally containing a small amount of food coloring as indicator), are equilibrated in a room at 22±2° C. The measurement is carried out at this same temperature.

The foam strip is saturated in water, then positioned vertically such that the lower end is immersed 1–2 mm in a reservoir of water. The water is allowed to drain from the sample until equilibrium is reached, typically 16–24 hours. During this procedure, the sample and reservoir should be shielded, for example by using a glass cylinder and aluminum foil, to prevent water loss due to evaporation. The sample is then quickly removed and placed on a non-absorbent surface where it is cut into 2.5 cm segments after discarding the portion of the sample that was immersed in the reservoir. Each piece is weighed, washed with water, dried and then reweighed. The absorbent capacity is calculated for each piece.

A capillary desorption isotherm curve is generated by plotting the absorbent capacity of each segment as a function of height. The curve is a plot of the absorbent capacity of each segment as a function of height that the test fluid desorbed, using the distance from the top of the water reservoir to the midpoint of each segment for the height h. The capillary desorption pressure is taken as the height of the foam that has an absorbent capacity one-half of the foam's free absorbent capacity.

C. Resistance to Compression Deflection (RTCD)

Resistance to compression deflection can be quantified by measuring the amount of strain (% reduction in thickness) produced in a foam sample which has been saturated with synthetic urine, after a confining pressure of 0.74 psi (5.1 kPa) has been applied to the sample. Resistance to Compression Deflection measurements are typically made on the same sample concurrently with the measurement of Free Absorbent Capacity as described below.

Jayco synthetic urine used in this method is prepared by dissolving a mixture of 2.0 g KCl, 2.0 g $Na_2SO_4$, 0.85 g $NH_4H_2PO_4$, 0.15 g $(NH_4)_2HPO_4$, 0.19 g $CaCl_2$, and 0.23 g $MgCl_2$ to 1.0 liters with distilled water. The salt mixture can be purchased from Endovations, Reading, Pa. (cat No. JA-00131-000-01).

The foam samples, Jayco synthetic urine and equipment used to make measurements are all equilibrated to a temperature of 31° C. All measurements are also performed at this temperature.

A foam sample sheet is saturated to its free absorbent capacity by soaking in a bath of Jayco synthetic urine. After 3 minutes, a cylinder having a 1 $in^2$ (6.5 $cm^2$) circular surface area is cut out of the saturated sheet with a sharp circular die. The cylindrical sample is soaked in synthetic urine at 31° C. for a further 6 minutes. The sample is then removed from the synthetic urine and is placed on a flat granite base under a gauge suitable for measuring the sample thickness. The gauge is set to exert a pressure of 0.08 psi (0.55 kPa) on the sample. Any gauge fitted with a foot having a circular surface area of at least 1 $in^2$ (6.5 $cm^2$) and capable of measuring thickness to 0.001 in (0.025 mm) can be employed. Examples of such gauges are an Ames model 482 (Ames Co.; Waltham, Mass.) or an Ono-Sokki model EG-225 (Ono-Sokki Co., Ltd.; Japan).

After 2 to 3 min., the expanded thickness (X1) is recorded. A force is then applied to the foot so that the saturated foam sample is subjected to a pressure of 0.74 psi (5.1 kPa) for 15 minutes. At the end of this time, the gauge is used to measure the final sample thickness (X2). From the initial and final thickness measurements, the percent strain induced can be calculated for the sample as follows: [(X1−X2)/X1]×100=% reduction in thickness.

D. Recovery from Wet Compression (RFWC)

The foam samples, Jayco synthetic urine and equipment used to make measurements are all equilibrated at 31° C. and 50% relative humidity. All measurements are also performed at this temperature and humidity. Thickness measurements are performed under a pressure of about 0.08 psi (0.55 kPa) using a gauge such as an Ames model 482 or an Ono-Sokki model EG-225.

A foam cylinder about 2 mm thick and 29 mm diameter is punched out of a sheet of foam. It is saturated to its free absorbent capacity in Jayco synthetic urine, then placed on top of three sheets of 9 cm diameter Whatman Grade No. 3 filter paper (particle retention: 6 μm). The role of the filter paper is to simulate the high absorption pressures typically associated with storage components in absorbent articles.

The foam/paper composite is immediately compressed 75% of the thickness of the wet foam (1.5 mm for a 2 mm thick sample) using a rigid plate larger in area than the foam sample. This strain is maintained for five minutes, during which time most of the synthetic urine is partitioned out of the foam and into the filter paper. After the five minute period, the confining plate is removed from the foam/paper composite, and the foam is given the opportunity to imbibe air and reexpand. Two minutes after removing the confining plate, the sample is separated from the paper and its thickness measured. The extent to which the sample recovers its thickness, expressed as a percentage of its initial thickness, is taken as a measure of the recovery from wet compression of the sample. The average of at least three measurements are used to determine RFWC.

E. Free Absorbent Capacity (FAC)

Free absorbent capacity can be quantified by measuring the amount synthetic urine absorbed in a foam sample which has been saturated with synthetic urine. Free Absorbent Capacity measurements are typically made on the same sample concurrently with the measurement of Resistance to Compression Deflection.

The foam samples and Jayco synthetic urine are equilibrated to a temperature of 31° C. Measurements are performed at ambient temperature.

A foam sample sheet is saturated to its free absorbent capacity by soaking in a bath of Jayco synthetic urine. After 3 minutes, a cylinder having a 1 $in^2$ (6.5 $cm^2$) circular surface area is cut out of the saturated, expanded sheet with a sharp circular die. The cylindrical sample is soaked in synthetic urine at 31° C. for a further 3 minutes. The sample is then removed from the synthetic urine and is placed on a digital balance. Any balance fitted with a weighing pan having an area larger than that of the sample and with a resolution of 1 milligram or less can be employed. Examples of such balances are the Mettler PM 480 and Mettler PC 440 (Mettler Instrument Corp; Hightstown N.J.).

After determining the weight of the wet foam sample (Ww), it is placed between 2 fine plastic mesh screens on top of 4 disposable paper towels. The sample is squeezed 3 times by firmly rolling a plastic roller over the top screen. The sample is then removed, soaked in distilled water for approximately 2 minutes, and squeezed between mesh screens as before. It is then placed between 8 layers of disposable paper towels (4 on each side) and pressed with 20,000 lbs. of force in a Carver Laboratory Press. The sample is then removed from the paper towels, dried in an oven at 82° C. for 20 minutes, and its dry weight recorded (Wd).

The free absorbent capacity (FAC) is the wet weight (Ww), less the dry weight (Wd) divided by the dry weight (Wd), i.e., FAC=[(Ww−Wd)/Wd].

F. Dynamic Mechanical Analysis (DMA)

DMA is used to determine the Tgs of polymers including polymeric foams. Samples of the foams are sliced into blocks 3–5 mm in thickness and washed 3–4 times in distilled water, expressing the fluid through roller nips between each washing. The resulting foam blocks are allowed to dry in air. The dried foam slices are cored to yield a cylinders 25 mm in diameter. These cylinders are analyzed using a Rheometrics RSA-II dynamic mechanical analyzer set in compression mode using parallel plates 25 mm in diameter. Instrument parameters used were as follows:

Temperature step from ca. 85° C. to 40° C. in steps of 2.5° C.

Soak intervals between temperature changes of 125–160 seconds

Dynamic strain set at 0.1% to 1.0% (usually 0.7%)

Frequency set at 1.0 radians/second

Autotension set in static force tracking dynamic force mode with initial static force set at 5 g.

The glass transition temperature is taken as the maximum point of the loss tangent versus temperature curve.

G. Interfacial Tension (IFT) Method (Spinning Drop)

Interfacial Tension (IFT) is measured at 50° C. by the spinning drop method described in copending U.S. application Ser. No. 989,270 (Dyer et al), filed Dec. 11, 1992 (herein incorporated by reference), except that: (1) the monomer mixture used in preparing the oil phase contains styrene, divinylbenzene (55% technical grade), 2-ethylhexylacrylate, and 1,4-butanediol dimethacrylate in a weight ratio of 14:14:60:12; (2) the concentration of emulsifier in the oil phase is varied by dilution from an upper concentration of generally about 5–10 weight % down to a concentration where the IFT increases to a value that is at least about 10 dyne/cm greater than the minimum IFT, or about 18 dyne/cm, whichever is less; (3) a smooth line drawn through a plot of IFT versus log emulsifier concentration is used to determine the minimum IFT; (4) the Critical Aggregation Concentration (CAC) is determined by extrapolating the low-concentration, generally linear portion of the IFT versus log concentration plot (i.e., the portion of the curve typically used to calculate surface area per molecule at the interface, see for example Surfactants and Interfacial Phenomena, Second Edition, Milton J. Rosen, 1989, Pages 64–69) to higher concentration; the emulsifier concentration on this extrapolated line corresponding to the minimum IFT is taken as the CAC. Generally, an upper emulsifier concentration of about 5–10 weight % is used. Desirably, the upper emulsifier concentration used is at least about twice (more desirably at least about three times) the CAC of the emulsifier. For emulsifiers having a solubility in the oil phase at ambient-temperature of less than 5 wt. %, the upper concentration limit can be reduced as long as this concentration is still at least about twice the CAC of the emulsifier at 50° C.

V. Specific Examples

These examples illustrate the specific preparation of collapsed HIPE foams according to the present invention.

EXAMPLE 1

Preparation of Foam from a HIPE

A) HIPE Preparation

Anhydrous calcium chloride (36.32 kg) and potassium persulfate (567 g) are dissolved in 378 liters of water. This provides the water phase stream to be used in a continuous process for forming a HIPE emulsion.

To a monomer combination comprising styrene (1600 g), divinylbenzene 55% technical grade (1600 g), 2-ethylhexylacrylate (4800 g) is added high purity diglycerol monooleate (480 g) and Tinuvin 765 [bis(1,2,2,5,5-pentamethylpiperidinyl)sebacate] antioxidant (40 g).

This diglycerol monooleate emulsifier is prepared following the general procedure for preparing polyglycerol esters described in copending U.S. application Ser. No. 989,270 (Dyer et al), filed Dec. 11, 1992. A polyglycerol composition comprising approximately 97% or greater diglycerol and 3% or less triglycerol (Solvay Performance Chemicals; Greenwich, Conn.) is esterified with fatty acids having a fatty acid composition comprising approximately 71% C18:1, 4% C18:2, 9% C16:1, 5% C16:0, and 11% other fatty acids (Emersol-233LL; Emery/Henkel) in a weight ratio of approximately 60:40, using sodium hydroxide as a catalyst at about 225° C. under conditions of mechanical agitation, nitrogen sparging, and gradually increasing vacuum, with subsequent phosphoric acid neutralization, cooling to about 85° C., and settling to reduce the level of unreacted polyglycerols. The polyglycerol ester reaction product is first fractionally distilled through two CMS-15A centrifugal molecular stills connected in series to reduce the levels of unreacted polyglycerols and fatty acids and then redistilled through the stills to yield distillation fractions high in diglycerol monoesters. Typical conditions for the final distillation pass are a feed rate of about 15 lb/hr, a degasser vacuum of about 21–26 microns, a bell jar vacuum of about 6–12 microns, a feed temperature of about 170° C., and a residue temperature of about 180° C. Distillation fractions high in diglycerol monoesters are combined, yielding a reaction product (as determined by supercritical fluid chromatography) comprising approximately 50% diglycerol monooleate, 27% other diglycerol monoesters, 20% polyglycerols, and 3% other polyglycerol esters. The resultant diglycerol monooleate emulsifier imparts a minimum oil phase/water phase interfacial tension value of approximately 1.0 dyne/cm and has a critical aggregation concentration of approximately 0.9 wt %. After mixing, the reaction product is allowed to settle overnight. The supernatant is withdrawn and used in the oil phase as the emulsifier in forming the HIPE. (About 20 g of a sticky residue is discarded.)

Separate streams of the oil phase (25° C.) and water phase (70°–74° C.) are fed to a dynamic mixing apparatus. Thorough mixing of the combined streams in the dynamic mixing apparatus is achieved by means of a pin impeller. At this scale of operation, an appropriate pin impeller comprises a cylindrical shaft of about 21.6 cm in length with a diameter of about 1.9 cm. The shaft holds 4 rows of pins, 2 rows having 17 pins and 2 rows having 16 pins, each having a diameter of 0.5 cm extending outwardly from the central axis of the shaft to a length of 1.6 cm. The pin impeller is mounted in a cylindrical sleeve which forms the dynamic mixing apparatus, and the pins have a clearance of 0.8 mm from the walls of the cylindrical sleeve.

A spiral static mixer is mounted downstream from the dynamic mixing apparatus to provide back pressure in the dynamic mixer and to provide improved incorporation of components into the emulsion that is eventually formed. Such a static mixer is 14.0 inches (35.6 cm) long with a 0.5 inch (1.3 cm) outside diameter. The static mixer is a TAH Industries Model 070-821, modified by cutting off 2.4 inches (6.1 cm).

The combined mixing apparatus set-up is filled with oil phase and water phase at a ratio of 2 parts water to 1 part oil. The dynamic mixing apparatus is vented to allow air to escape while filling the apparatus completely. The flow rates during filling are 3.78 g/sec oil phase and 7.56 cc/sec water phase.

Once the apparatus set-up is filled, agitation is begun in the dynamic mixer, with the impeller turning at 1200 RPM. The flow rate of the water phase is then steadily increased to a rate of 44.1 cc/sec in a time period of about 30 sec. and the oil phase flow rate is reduced to 1.25 g/sec over a time period of about 1 min. The back pressure created by the dynamic and static mixers at this point is 5.0 PSI (35 kPa). The impeller speed is then steadily decreased to a speed of 600 RPM over a period of 120 sec. The system back pressure decreases to 1.8 PSI (12 kPa) and remains constant thereafter. The resultant HIPE has a water-to-oil ratio of about 36:1.

B) Polymerization/Curing of HIPE

The HIPE from the static mixer is collected in a round polypropylene tub, 17 in (43 cm) in diameter and 7.5 in (10 cm) high, with a concentric insert made of Celcon plastic. The insert is 5.0 in (12.7 cm) in diameter at its base and 4.75 in (12 cm) in diameter at its top and is 6.75 in (17.1 cm) high. The HIPE-containing tubs are kept in a room maintained at 65° C. for 18 hours to cure and provide a polymeric HIPE foam.

C) Foam Washing and Dewatering

The cured HIPE foam is removed from the tubs. The foam at this point has residual water phase (containing dissolved emulsifiers, electrolyte, initiator residues, and initiator) about 32–38 times (32–38X) the weight of polymerized monomers. The foam is sliced with a sharp reciprocating saw blade into sheets which are 0.075 inches (0.19 cm) in thickness. These sheets are then subjected to compression in a series of 2 porous nip rolls equipped with vacuum which gradually reduces the residual water phase content of the foam to about 2 times (2X) the weight of the polymerized monomers. At this point, the sheets are then resaturated with a 0.75% $CaCl_2$ solution at 60° C., are squeezed in a series of 3 porous nip rolls equipped with vacuum to a water phase content of about 4X. The $CaCl_2$ content of the foam is between 2 and 5%.

The HIPE foam is then dried in air for about 16 hours. Such drying reduces the moisture content to about 4–10% by weight of polymerized material.

EXAMPLE 2

Preparation of Foam from a HIPE

A) HIPE Preparation

Anhydrous calcium chloride (36.32 kg) and potassium persulfate (189 g) are dissolved in 378 liters of water. This provides the water phase stream to be used in a continuous process for forming a HIPE emulsion.

To a monomer combination comprising styrene (600 g) technical grade divinylbenzene (700 g), 2-ethylhexylacrylate (3100 g), and 1,4 butanediol dimethacrylate (600 g) is added diglycerol monooleate (250 g), 2-octyldodecyl diglycerol ether (50 g) and Tinuvin 765 (41 g) antioxidant (30 g).

The diglycerol monooleate emulsifier is the same as that used in Example 1. The 2-octyldodecyl diglycerol ether coemulsifier is prepared as follows: 2-Octyldodecyl glycidyl ether is prepared using the aliphatic glycidyl ether method described in copending U.S. application Ser. No. 08/514,346 (Stephen A. Goldman et al), filed Aug. 9, 1995, which is incorporated by reference. Approximately 360 g of epichlorohydrin is added to a stirred mixture of about 1.5 kg of 2-octyldodecanol (Jarcol I-20; Jarchem Industries) and about 10 g of stannic chloride. After the resulting exotherm heats the reaction mixture to about 70° C., the mixture is stirred under nitrogen for an additional about 6 hours at about 65° C. About 190 g of sodium hydroxide prediluted in approximately 28 g of distilled water is then added and reacted for about 6 hours at about 65° C. After separating the aqueous layer, the organic layer is water washed three times, heated to about 95° C., sparged with nitrogen to dry, and distilled in the range of about 185°–210° C. and <1 mm Hg to yield approximately 1.1 kg of 2-octyldodecyl glycidyl ether. Approximately 8.1 g of sodium methoxide (25% by weight in methanol) and approximately 1400 g of anhydrous glycerine are reacted together for about 3 hours under nitrogen at about 130° C. After heating the resulting mixture to about 185° C., the 2-octyldodecyl glycidyl ether is added dropwise over a period of about 2 hours. The resultant mixture is stirred for about 4 hours at about 185° C. under nitrogen and then allowed to cool without mixing. A glycerine layer settles to the bottom and is removed by siphoning. Volatiles are distilled from the remaining material by heating to about 150° C. at about 2 mm Hg, yielding approximately 1.3 kg of product. Approximately 700 g of the product is dissolved into an excess of mixed hexanes. This hexane phase is multiply extracted with 90:10 (v:v) methanol:water. The methanol:water extracts are combined and the solvent is removed using a rotary evaporator. The resulting residue is heated to about 70° C. and filtered through a glass microfiber filter, yielding approximately 380 g of 2-octyldodecyl diglycerol ether emulsifier. The product is analyzed by gel permeation chromatography and found to be about 82% diglycerol monoaliphatic ether and about 5% triglycerol dialiphatic ether. It imparts a minimum oil phase/water phase interfacial tension value of approximately 3.9 dyne/cm and has a critical aggregation concentration of approximately 0.5 wt %.

After mixing, this combination of materials is allowed to settle overnight. No visible residue was formed and all of the mix was withdrawn and used as the oil phase in a continuous process for forming a HIPE emulsion.

At an aqueous phase temperature of 85°–90° C. and an oil phase temperature of 23° C., separate streams of the oil phase and water phase are fed to a dynamic mixing apparatus. Thorough mixing of the combined streams in the dynamic mixing apparatus is achieved by means of a pin impeller, as in Example 1. As in Example 1, spiral static mixer is also mounted downstream from the dynamic mixing apparatus to provide back pressure and improved incorporation of components into the emulsion that is eventually formed. The combined mixing apparatus set-up is filled with oil phase and water phase at a ratio of 2 parts water to 1 part oil. The dynamic mixing apparatus is vented to allow air to escape while filling the apparatus completely. The flow rates during filling are 3.78 g/sec oil phase and 7.56 cc/sec water phase.

Once the apparatus set-up is filled, the water phase flow rate is cut by 25% to reduce the pressure build up while the vent is closed. Agitation is then begun in the dynamic mixer, with the impeller turning at 1800 RPM. The flow rate of the water phase is then steadily increased to a rate of 37.8 cc/sec over a time period of about 1 minute and the oil phase flow rate is reduced to 0.84 g/sec over a time period of about 2 minutes. When the water phase flow rate reaches 37.8 cc/sec, the impeller speed is instantly reduced to 1200 RPM and then steadily reduced over a period of 1 min to 900 RPM. The back pressure created by the dynamic and static mixers at this point is about 2.3 PSI (16 kPa). The impeller speed is then reduced steadily to about 850 RPM over a period of 1 minute. The back pressure created by the dynamic and static mixers at this point is about 2.2 PSI (15 kPa). The resultant HIPE has a water-to-oil ratio of about 45:1.

B) Polymerization of the Emulsion

The formed emulsion flowing from the static mixer at this point is collected in round polypropylene tubs, as in Example 1. The emulsion-containing tubs are kept in a room maintained at 82° C. for 4 hours to bring about polymerization of the emulsion in the containers to thereby form polymeric foam.

C) Foam Washing and Dewatering

After curing is complete, the wet cured foam is removed from the curing tubs. The foam at this point contains about 40–50 times the weight of polymerized material (40–50X) of the residual water phase containing dissolved emulsifiers, electrolyte, initiator residues, and initiator. The foam is sliced with a sharp reciprocating saw blade into sheets which are 0.075 inches (0.19 cm) in thickness. These sheets are then subjected to compression in a series of 2 porous nip rolls equipped with vacuum which gradually reduce the residual water phase content of the foam to about 3 times (3X) the weight of the polymerized material. At this point, the sheets are then resaturated with a 1.5% $CaCl_2$ solution at 60° C., are squeezed in a series of 3 porous nip rolls equipped with vacuum to a water phase content of about 1X. The $CaCl_2$ content of the foam is between 2 and 5%.

The foam is then dried in air for about 16 hours. Such drying reduces the moisture content to about 4–10% by weight of polymerized material.

EXAMPLE 3

Preparation of Foam from a HIPE

A) HIPE Preparation

Anhydrous calcium chloride (36.32 kg) and potassium persulfate (1.13 kg) are dissolved in 378 liters of water. This provides the water phase stream to be used in a continuous process for forming a HIPE emulsion.

To a monomer combination comprising distilled divinylbenzene (40% divinylbenzene and 60% ethyl styrene) (1750 g), 2-ethylhexylacrylate (2750 g), and 1,4 hexanediol diacrylate (500 g) is added diglycerol monooleate (250 g), dihydrogenated tallow dimethyl ammonium methylsulfate (50 g) and Tinuvin 765 antioxidant (25 g). The diglycerol monooleate emulsifier (Grindsted Products; Brabrand, Denmark) comprises approximately 82% diglycerol monooleate, 1% other diglycerol monoesters, 7% polyglycerols, and 11% other polyglycerol esters, imparts a minimum oil phase/water phase interfacial tension value of approximately 2.4 dyne/cm, and has a critical aggregation concentration of approximately 3.0 wt %. The dihydrogenated tallow dimethyl ammonium methyl sulfate is obtained from Witco/Sherex Chemical Co. It imparts a minimum oil phase/water phase interfacial tension value of approximately 2.5 dyne/cm and has a critical aggregation concentration of approximately 0.065 wt %. After mixing, this combination of materials is allowed to settle overnight. Only a small visible residue was formed and nearly all of the mix was withdrawn and used as the oil phase in a continuous process for forming a HIPE emulsion.

At an aqueous phase temperature of 85°–90° C. and an oil phase temperature of 20° C., separate streams of the oil phase and water phase are fed to a dynamic mixing apparatus. Thorough mixing of the combined streams in the dynamic mixing apparatus is achieved by means of a pin impeller, as in Example 1. As in Example 1, spiral static mixer is also mounted downstream from the dynamic mixing apparatus to provide back pressure and improved incorporation of components into the emulsion that is eventually formed. The combined mixing apparatus set-up is filled with oil phase and water phase at a ratio of 2 parts water to 1 part oil. The dynamic mixing apparatus is vented to allow air to escape while filling the apparatus completely. The flow rates during filling are 3.78 g/sec oil phase and 7.6 cc/sec water phase.

Once the apparatus set-up is filled, the water phase flow rate is cut by 25% to reduce the pressure build up while the vent is closed. Agitation is then begun in the dynamic mixer, with the impeller turning at 1200 RPM. The flow rate of the water phase is then steadily increased to a rate of 37.8 cc/sec over a time period of about 1 minute and the oil phase flow rate is reduced to 0.63 g/sec over a time period of about 3 minutes. The back pressure created by the dynamic and static mixers at this point is about 3 PSI (21 kPa). The impeller speed is steadily reduced to 800 RPM over a period of about 2 minutes and the back pressure drops to about 2.3 PSI (16 kPa). The resultant HIPE has a water-to-oil ratio of about 60:1.

B) Polymerization of the Emulsion

The formed emulsion flowing from the static mixer at this point is collected in round polypropylene tubs, as in Example 1. The emulsion-containing tubs are kept in a room maintained at 82° C. for 2 hours to bring about polymerization of the emulsion in the containers to thereby form polymeric foam.

C) Foam Washing and Dewatering

After curing is complete, the wet cured foam is removed from the curing tubs. The foam at this point contains about 50–60 times the weight of polymerized material (50–60X) of the residual water phase containing dissolved emulsifiers, electrolyte, initiator residues, and initiator. The foam is sliced with a sharp reciprocating saw blade into sheets which are 0.050 inches (0.127 cm) in thickness. These sheets are then subjected to compression in a series of 2 porous nip rolls equipped with vacuum which gradually reduce the residual water phase content of the foam to about 3 times (3X) the weight of the polymerized material. At this point, the sheets are then resaturated with a 1.5% $CaCl_2$ solution at 60° C., are squeezed in a series of 3 porous nip rolls equipped with vacuum to a water phase content of about 1X. The $CaCl_2$ content of the foam is between 1 and 4%.

The foam is then dried in air for about 16 hours. Such drying reduces the moisture content to about 3–12% by weight of polymerized material.

What is claimed is:

1. A polymeric foam material which is capable of acquiring and distributing aqueous fluids, said polymeric foam material comprising a hydrophilic, flexible, nonionic polymeric foam structure of interconnected open cells, which foam structure has:

A) the ability to vertically wick synthetic urine to a height of 5 cm in less than about 120 seconds;

B) a capillary absorption pressure of from about 5 to about 25 cm;

C) a capillary desorption pressure of from about 8 to about 40 cm;

D) a resistance to compression deflection of from about 5 to about 85% when measured under a confining pressure of 0.74 psi;

E) a free absorbent capacity of from about 12 to about 125 g/g;

F) a recovery from wet compression of at least about 60%.

2. The foam material of claim 1 wherein said foam structure has:

A) the ability to vertically wick synthetic urine to a height of 5 cm in less than about 70 seconds;

B) a capillary absorption pressure of from about 5 to about 15 cm;

C) a capillary desorption pressure of from about 8 to about 25 cm;

D) a resistance to compression deflection of from about 5 to about 65%

E) a free absorbent capacity of from about 35 to about 90 g/g;

F) a recovery from wet compression of at least about 75%.

3. The foam material of claim 2 wherein said foam structure has a free absorbent capacity of from about 45 to about 75 g/g, and a recovery from wet compression of at least about 90%.

4. The foam material of claim 2 wherein said foam structure has a resistance to compression deflection of from about 5 to about 50%.

5. The foam material of claim 1 which has a number average cell size of from about 20 to about 200 μm and a number average hole size of from about 5 to about 30 μm.

6. The foam material of claim 5 wherein said cell size is from about 30 to about 130 μm and wherein said hole size is from about 8 to about 25 μm.

7. The foam material of claim 1 wherein said foam structure has a specific surface area per foam volume of from about 0.01 to about 0.06 m$^2$/cc.

8. The foam material of claim 2 wherein said foam structure has a specific surface area per foam volume of from about 0.01 to about 0.04 m$^2$/cc.

9. The foam material of claim 1 which is made from a polymerized water-in-oil emulsion having:

1) an oil phase comprising:

a) from about 85 to about 98% by weight of a monomer component capable of forming a copolymer having a Tg value of below about 35° C. or lower, said monomer component comprising:

i) from about 30 to about 80% by weight of a substantially water-insoluble, monofunctional monomer capable of forming a polymer having a Tg of about 25° C. or less;

ii) from about 5 to about 40% by weight of a substantially water-insoluble, monofunctional comonomer capable of imparting toughness about equivalent to that provided by styrene;

iii) from about 5 to about 25% by weight of a first substantially water-insoluble, polyfunctional crosslinking agent selected from the group consisting of divinylbenzenes, trivinylbenzenes, divinyltoluenes, divinylxylenes, divinylnaphthalenes divinylalkylbenzenes, divinylphenanthrenes, divinylbiphenyls, divinyldiphenylmethanes, divinylbenzyls, divinylphenylethers, divinyldiphenylsulfides, divinylfurans, divinylsulfide, divinylsulfone, and mixtures thereof, and iv) from 0 to about 15% by weight of a second substantially water-insoluble, polyfunctional crosslinking agent selected from the group consisting of polyfunctional acrylates, methacrylates, acrylamides, methacrylamides, and mixtures thereof, b) from about 2 to about 15% by weight of an emulsifier component which is soluble in the oil phase and which is suitable for forming a stable water-in-oil emulsion; and 2) a water phase comprising from about 0.2 to about 20% by weight of a water-soluble electrolyte;

3) a volume to weight ratio of water phase to oil phase in the range of from about 35:1 to about 90:1.

10. The foam material of claim 9 wherein:

1) the oil phase comprises:

a) from about 90 to about 97% by weight of a monomer component capable of forming a copolymer having a Tg value from about 15° to about 30° C., said monomer component comprising:

i) from about 50 to about 65% by weight monomer selected from the group consisting of $C_4$–$C_{14}$ alkyl acrylates, aryl and alkaryl acrylates, $C_6$–$C_{16}$ alkyl methacrylates, $C_4$–$C_{12}$ alkyl styrenes, acrylamides and mixtures thereof;

ii) from about 15 to about 25% by weight comonomer selected from the group consisting of styrene, ethyl styrene and mixtures thereof;

iii) from about 12 to about 20% by weight divinylbenzene; and iv) from 0 to about 13% by weight of said second crosslinking agent selected from the group consisting of 1,4-butanediol dimethacrylate, ethylene glycol dimethacrylate, 1,6-hexanediol diacrylate, and mixtures thereof;

b) from about 3 to about 10% by weight of said emulsifier component;

2) the water phase comprises from about 1 to about 10% calcium chloride;

3) the volume to weight ratio of water phase to oil phase is in the range of from about 45:1 to about 75:1.

11. The foam material of claim 10 wherein said monomer (i) is selected from the group consisting of butyl acrylate, hexyl acrylate, octyl acrylate, 2-ethylhexyl acrylate, nonyl acrylate, decyl acrylate, dodecyl acrylate, isodecyl acrylate, tetradecyl acrylate, benzyl acrylate, nonylphenyl acrylate, hexyl methacrylate, octyl methacrylate, nonyl methacrylate, decyl methacrylate, isodecyl methacrylate, dodecyl methacrylate, tetradecyl methacrylate, p-n-octylstyrene, N-octadecyl acrylamide, and mixtures thereof.

* * * * *

UNITED STATES PATENT AND TRADEMARK OFFICE
CERTIFICATE OF CORRECTION

PATENT NO. : 5,786,395

DATED : July 28, 1998

INVENTOR(S) : Keith Joseph Stone, et al.

It is certified that error appears in the above-identified patent and that said Letters Patent is hereby corrected as shown below:

On the title page, item [75] Inventor, delete "Michelle Renee Peace" and insert item [56] References Cited.

U. S. PATENT DOCUMENTS

| DOCUMENT NUMBER | DATE | NAME | CLASS | SUB CLASS |
|---|---|---|---|---|
| 3,255,127 | 6/7/66 | Leverkusen et al | 260 | 2.5 |
| 3,256,219 | 6/14/66 | Will | 260 | 2.5 |
| 3,431,911 | 6/17/66 | Meisel, Jr. | 128 | 287 |
| 3,563,243 | 2/16/71 | Lindquist | 128 | 287 |
| 3,565,817 | 2/23/71 | Lissant | 252 | 312 |
| 3,640,753 | 2/8/72 | Krauch et al | 117 | 62.2 |
| 3,734,867 | 5/22/73 | Will | 260 | 2.5 R |
| 3,763,056 | 6/2/71 | Will | 260 | 2.5 L |
| 3,778,390 | 12/11/73 | Ulrich, Jr | 260 | 2.5 AN |
| 3,806,474 | 4/23/74 | Blair | 260 | 2.5 AG |
| 3,988,508 | 10/26/76 | Lissant | 526 | 344 |
| 3,993,074 | 11/23/76 | Murray et al | 128 | 286 |
| 3,994,298 | 11/30/76 | DesMarais | 128 | 285 |
| 4,029,100 | 6/14/77 | Karami | 128 | 284 |
| 4,049,592 | 9/20/77 | Marans et al | 260 | 2.5 AD |
| 4,061,145 | 12/6/77 | DesMarais | 128 | 275 |
| 4,067,832 | 1/10/78 | DesMarais | 260 | 2.5 AB |
| 4,093,570 | 6/6/78 | Miyake et al | 260 | 2.5 B |
| 4,110,276 | 8/29/78 | DesMarais | 521 | 123 |
| 4,132,839 | 1/2/79 | Marans et al | 521 | 159 |
| 4,262,052 | 4/14/81 | Kannan et al | 428 | 306 |
| 4,376,440 | 3/25/83 | Whitehead et al | 604 | 387 |
| 4,394,930 | 7/26/83 | Korpman | 220 | 444 |
| 4,425,130 | 1/10/84 | DesMarais | 604 | 389 |

UNITED STATES PATENT AND TRADEMARK OFFICE
CERTIFICATE OF CORRECTION

PATENT NO. : 5,786,395

DATED : July 28, 1998

INVENTOR(S) : Keith Joseph Stone, et al.

It is certified that error appears in the above-identified patent and that said Letters Patent is hereby corrected as shown below:

U. S. PATENT DOCUMENTS

| | | | | |
|---|---|---|---|---|
| 4,473,611 | 9/25/84 | Haq | 428 | 198 |
| 4,522,953 | 6/11/85 | Barby et al | 521 | 64 |
| 4,536,521 | 8/20/85 | Haq | 521 | 146 |
| 4,540,717 | 9/10/85 | Mahnke et al | 521 | 52 |
| 4,554,297 | 11/19/85 | Dabi | 521 | 178 |
| 4,603,069 | 7/29/86 | Haq et al | 428 | 76 |
| 4,603,069 | 7/29/86 | Haq et al | 428 | 76 |
| 4,606,958 | 8/19/86 | Haq et al | 428 | 68 |
| 4,611,014 | 9/9/86 | Jones et al | 521 | 146 |
| 4,612,334 | 9/16/86 | Jones et al | 521 | 146 |
| 4,613,543 | 9/26/86 | Dabi | 428 | 304.4 |
| 4,668,709 | 5/26/87 | Jones et al | 521 | 146 |
| 4,724,242 | 2/9/88 | Vassileff | 521 | 83 |
| 4,725,628 | 2/16/88 | Garvey et al | 521 | 137 |
| 4,731,391 | 3/15/88 | Garvey | 521 | 137 |
| 4,740,528 | 4/26/88 | Garvey et al | 521 | 128 |
| 4,775,655 | 10/4/88 | Edwards et al | 502 | 416 |
| 4,788,225 | 11/29/88 | Edwards et al | 521 | 147 |
| 4,797,310 | 1/10/89 | Barby et al | 428 | 71 |
| 4,839,395 | 6/13/89 | Masamizu et al | 521 | 56 |
| 4,957,810 | 9/18/90 | Eleouet et al | 428 | 306.6 |
| 4,959,341 | 9/25/90 | Wallach | 502 | 404 |
| 4,961,982 | 10/9/90 | Taylor | 428 | 41 |
| 4,965,289 | 10/23/90 | Sherrington et al | 521 | 53 |
| 4,966,919 | 10/30/90 | Williams Jr. et al | 521 | 54 |
| 4,985,467 | 1/15/91 | Kelly et al | 521 | 52 |
| 4,985,468 | 1/15/91 | Elmes et al | 521 | 63 |

UNITED STATES PATENT AND TRADEMARK OFFICE
CERTIFICATE OF CORRECTION

PATENT NO. : 5,786,395

DATED : July 28, 1998

INVENTOR(S) : Keith Joseph Stone, et al.

It is certified that error appears in the above-identified patent and that said Letters Patent is hereby corrected as shown below:

U. S. PATENT DOCUMENTS

| DOCUMENT NUMBER | DATE | NAME | CLASS | SUB CLASS |
|---|---|---|---|---|
| 4,990,541 | 2/5/91 | Nielsen et al | 521 | 70 |
| 4,992,254 | 2/12/91 | Kong | 423 | 449 |
| 5,021,462 | 6/4/91 | Elmes et al | 521 | 63 |
| 5,037,859 | 8/6/91 | Williams, Jr. et al | 521 | 55 |
| 5,047,225 | 9/10/91 | Kong | 423 | 447.2 |
| 5,065,752 | 11/19/91 | Sessions et al | 128 | 156 |
| 5,066,684 | 11/19/91 | LeMay | 521 | 64 |
| 5,066,784 | 11/19/91 | Sherrington et al | 530 | 334 |
| 5,110,838 | 5/5/92 | Tokiwa et al | 521 | 81 |
| 5,116,880 | 5/26/92 | Tokiwa et al | 521 | 134 |
| 5,116,883 | 5/26/92 | LeMay | 521 | 178 |
| 5,128,382 | 7/7/92 | Elliott, Jr. et al | 521 | 178 |
| 5,134,007 | 7/28/92 | Reising et al | 428 | 78 |
| 5,134,171 | 7/28/92 | Hammel et al | 521 | 98 |
| 5,147,345 | 9/15/92 | Young et al | 604 | 378 |
| 5,149,720 | 9/22/92 | DesMarais et al | 521 | 63 |
| 5,189,070 | 2/23/93 | Brownscombe et al | 521 | 64 |
| 5,198,472 | 3/30/93 | DesMarais et al | 521 | 63 |
| 5,200,433 | 4/6/93 | Beshouri | 521 | 64 |
| 5,210,104 | 5/11/93 | Bass et al | 521 | 64 |
| 5,210,108 | 5/11/93 | Spinu et al | 521 | 182 |
| 5,221,726 | 6/22/93 | Dabi et al | 528 | 93 |
| 5,250,576 | 10/5/93 | DesMarais et al | 521 | 63 |
| 5,252,619 | 10/12/93 | Brownscombe et al | 521 | 64 |
| 5,260,345 | 11/9/93 | DesMarais et al | 521 | 148 |
| 5,268,224 | 12/7/93 | DesMarais et al | 428 | 286 |
| 5,290,820 | 3/1/94 | Brownscombe et al | 521 | 64 |
| 5,318,554 | 6/7/94 | Young et al | 604 | 378 |
| 5,331,015 | 7/19/94 | DesMarais et al | 521 | 62 |
| 5,336,208 | 8/9/94 | Rosenbluth et al | 604 | 329 |
| 5,336,695 | 8/9/94 | Nass et al | 521 | 109.1 |
| 5,352,711 | 10/4/94 | DesMarais | 521 | 149 |
| 5,387,207 | 2/7/95 | Dyer et al | 604 | 369 |

Page 3 of 5

UNITED STATES PATENT AND TRADEMARK OFFICE
CERTIFICATE OF CORRECTION

PATENT NO. : 5,786,395　　　　　　　　　　　　Page 4 of 5

DATED　　　: July 28, 1998

INVENTOR(S) : Keith Joseph Stone, et al.

It is certified that error appears in the above-identified patent and that said Letters Patent is hereby corrected as shown below:

FOREIGN PATENT DOCUMENTS

| DOCUMENT NUMBER | DATE | COUNTRY | CLASS | SUB CLASS | TRANSLATION YES | NO |
|---|---|---|---|---|---|---|
| WO 94/28839 | 12/22/94 | PCT | | | | |
| 0 017 671 A1 | 10/29/80 | Europe | | | | |
| 0 017 672 A1 | 10/29/80 | Europe | | | | |
| 0 049 768 A1 | 4/21/82 | Europe | | | | |
| 0 299 762 | 1/18/89 | Europe | | | | |
| 0 480 379 A2 | 4/15/92 | Europe | | | | |
| FR 1,340,520 | 9/9/63 | France | | | X | |
| 1 493 356 | 11/30/77 | Great Britian | | | | |
| 2 188 055 A | 9/23/87 | Great Britian | | | | |
| 3 109 929 A1 | 1/14/82 | German | | | | |
| 3-49759 | 3/4/91 | Japan | | | | |
| Hei 2-289608 | 11/29/90 | Japan | | | X | |
| Het 2-239863 | 9/21/90 | Japan | | | X | |

UNITED STATES PATENT AND TRADEMARK OFFICE
CERTIFICATE OF CORRECTION

PATENT NO. : 5,786,395

DATED : July 28, 1998

INVENTOR(S) : Keith Joseph Stone, et al.

It is certified that error appears in the above-identified patent and that said Letters Patent is hereby corrected as shown below:

OTHER DOCUMENTS

| |
|---|
| Structure of High Internal Phase Ratio Emulsions, Lissant, pgs 416-423, 1974 |
| A Study of Medium and High Internal Phase Ratio Water/Polymer Emulsions, Lissant, pgs 201-108, 1973 |
| The Geometry of High-Internal-Phase Ratio Emulsions, Lissant, pgs 462-468 1966 |
| Low Density, Microcellular polystyrene foams, Aubert and Clough, pgs 2047-2054, 1985 |
| Mechanical Structure Property Relationships of Microceliulsr, Low Density Foams, LeMay, pgs 21-26, 1991 |
| New Melamine-based elastic foam, Weber and Kruckau, pgs 843-848, 1985 |
| Preparation of multishell ICF target plastic foam cushion materials by thermally induced phase inversion processes, Young, Moreno and Marsters, pgs 1094-2004, 1981 |
| Cellular Solids Structure & Properties, Gibson and Ashby, pgs 120-200, 1988 |

Signed and Sealed this

Fifth Day of September, 2000

Attest:

Attesting Officer

Q. TODD DICKINSON

Director of Patents and Trademarks

UNITED STATES PATENT AND TRADEMARK OFFICE
CERTIFICATE OF CORRECTION

PATENT NO. : 5,786,395  
DATED : July 28, 1998  
INVENTOR(S) : K. J. Stone et al.

Page 1 of 4

It is certified that error appears in the above-identified patent and that said Letters Patent is hereby corrected as shown below:

Title page,  
Item [56], insert the following:  
Under "FOREIGN PATENT DOCUMENTS"

| | | |
|---|---|---|
| -- WO 94/28839 | 12/22/94 | PCT |
| 0 017 671 A1 | 10/29/80 | Europe |
| 0 017 672 A1 | 10/29/80 | Europe |
| 0 049 768 A1 | 4/21/82 | Europe |
| 0 299 762 | 1/18/89 | Europe |
| 0 480 379 A2 | 4/15/92 | Europe |
| FR 1,340,520 | 9/9/63 | France |
| 1 493 356 | 11/30/77 | Great Britian |
| 2 188 055 A | 9/23/87 | Great Britian |
| 3 109 929 A1 | 1/14/82 | German |
| 3-49759 | 3/4/91 | Japan |
| Hei 2-289608 | 11/29/90 | Japan |
| Het 2-239863 | 9/21/90 | Japan |

Under "OTHER PUBLICATIONS"  
Structure of High Internal Phase Ratio Emulsions, Lissant, pgs 416-423, 1974  
A Study of Medium and High Internal Phase Ratio Water/Polymer Emulsions, Lissant, pgs 201-108, 1973  
The Geometry of High-Internal-Phase Ratio Emulsions, Lissant, pgs 462-468 1966  
Low Density, Microcellular polystyrene foams, Aubert and Clough, pgs 2047-2054, 1985  
Mechanical Structure Property Relationships of Microcellulsr, Low Density Foams, LeMay, pgs 21-26, 1991  
New Melamine-based elastic foam, Weber and Kruckau, pgs 843-848, 1985  
Preparation of multishell ICF target plastic foam cushion materials by thermally induced phase inversion processes, Young, Moreno and Marsters, pgs 1094-2004, 1981  
Cellular Solids Structure & Properties, Gibson and Ashby, pgs 120-200, 1988

Under References Cited,  
U.S. PATENT DOCUMENTS

| | | |
|---|---|---|
| 3,255,127 | 6/7/66 | Leverkusen et al |
| 3,256,219 | 6/14/66 | Will |
| 3,431,911 | 6/17/66 | Meisel, Jr. |
| 3,563,243 | 2/16/71 | Lindquist |

UNITED STATES PATENT AND TRADEMARK OFFICE
CERTIFICATE OF CORRECTION

PATENT NO.    : 5,786,395
DATED         : July 28, 1998
INVENTOR(S)   : K. J. Stone et al.

It is certified that error appears in the above-identified patent and that said Letters Patent is hereby corrected as shown below:

| | | |
|---|---|---|
| 3,565,817 | 2/23/71 | Lissant |
| 3,640,753 | 2/8/72 | Krauch et al |
| 3,734,867 | 5/22/73 | Will |
| 3,763,056 | 6/2/71 | Will |
| 3,778,390 | 12/11/73 | Ulrich, Jr |
| 3,806,474 | 4/23/74 | Blair |
| 3,988,508 | 10/26/76 | Lissant |
| 3,993,074 | 11/23/76 | Murray et al |
| 3,994,298 | 11/30/76 | DesMarais |
| 4,029,100 | 6/14/77 | Karami |
| 4,049,592 | 9/20/77 | Marans et al |
| 4,061,145 | 12/6/77 | DesMarais |
| 4,067,832 | 1/10/78 | DesMarais |
| 4,093,570 | 6/6/78 | Miyake et al |
| 4,110,276 | 8/29/78 | DesMarais |
| 4,132,839 | 1/2/79 | Marans et al |
| 4,262,052 | 4/14/81 | Kannan et al |
| 4,376,440 | 3/25/83 | Whitehead et al |
| 4,394,930 | 7/26/83 | Korpman |
| 4,425,130 | 1/10/84 | DesMarais |
| 4,473,611 | 9/25/84 | Haq |
| 4,522,953 | 6/11/85 | Barby et al |
| 4,536,521 | 8/20/85 | Haq |
| 4,540,717 | 9/10/85 | Mahnke et al |
| 4,554,297 | 11/19/85 | Dabi |
| 4,603,069 | 7/29/86 | Haq et al |
| 4,603,069 | 7/29/86 | Haq et al |
| 4,606,958 | 8/19/86 | Haq et al |
| 4,611,014 | 9/9/86 | Jones et al |
| 4,612,334 | 9/16/86 | Jones et al |
| 4,613,543 | 9/26/86 | Dabi |
| 4,668,709 | 5/26/87 | Jones et al |
| 4,724,242 | 2/9/88 | Vassileff |
| 4,725,628 | 2/16/88 | Garvey et al |
| 4,731,391 | 3/15/88 | Garvey |
| 4,740,528 | 4/26/88 | Garvey et al |
| 4,775,655 | 10/4/88 | Edwards et al |
| 4,788,225 | 11/29/88 | Edwards et al |

UNITED STATES PATENT AND TRADEMARK OFFICE
CERTIFICATE OF CORRECTION

PATENT NO. : 5,786,395
DATED : July 28, 1998
INVENTOR(S) : K. J. Stone et al.

It is certified that error appears in the above-identified patent and that said Letters Patent is hereby corrected as shown below:

| | | |
|---|---|---|
| 4,797,310 | 1/10/89 | Barby et al |
| 4,839,395 | 6/13/89 | Masamizu et al |
| 4,957,810 | 9/18/90 | Eleouet et al |
| 4,959,341 | 9/25/90 | Wallach |
| 4,961,982 | 10/9/90 | Taylor |
| 4,965,289 | 10/23/90 | Sherrington et al |
| 4,966,919 | 10/30/90 | Williams Jr. et al |
| 4,985,467 | 1/15/91 | Kelly et al |
| 4,985,468 | 1/15/91 | Elmes et al |
| 4,990,541 | 2/5/91 | Nielsen et al |
| 4,992,254 | 2/12/91 | Kong |
| 5,021,462 | 6/4/91 | Elmes et al |
| 5,037,859 | 8/6/91 | Williams, Jr. et al |
| 5,047,225 | 9/10/91 | Kong |
| 5,065,752 | 11/19/91 | Sessions et al |
| 5,066,684 | 11/19/91 | LeMay |
| 5,066,784 | 11/19/91 | Sherrington et al |
| 5,110,838 | 5/5/92 | Tokiwa et al |
| 5,116,880 | 5/26/92 | Tokiwa et al |
| 5,116,883 | 5/26/92 | LeMay |
| 5,128,382 | 7/7/92 | Elliott, Jr. et al |
| 5,134,007 | 7/28/92 | Reising et al |
| 5,134,171 | 7/28/92 | Hammel et al |
| 5,147,345 | 9/15/92 | Young et al |
| 5,149,720 | 9/22/92 | DesMarais et al |
| 5,189,070 | 2/23/93 | Brownscombe et al |
| 5,198,472 | 3/30/93 | DesMarais et al |
| 5,200,433 | 4/6/93 | Beshouri |
| 5,210,104 | 5/11/93 | Bass et al |
| 5,210,108 | 5/11/93 | Spinu et al |
| 5,221,726 | 6/22/93 | Dabi et al |
| 5,250,576 | 10/5/93 | DesMarais et al |
| 5,252,619 | 10/12/93 | Brownscombe et al |
| 5,260,345 | 11/9/93 | DesMarais et al |
| 5,268,224 | 12/7/93 | DesMarais et al |
| 5,290,820 | 3/1/94 | Brownscombe et al |
| 5,318,554 | 6/7/94 | Young et al |

UNITED STATES PATENT AND TRADEMARK OFFICE
CERTIFICATE OF CORRECTION

PATENT NO.   : 5,786,395
DATED        : July 28, 1998
INVENTOR(S)  : K. J. Stone et al.

It is certified that error appears in the above-identified patent and that said Letters Patent is hereby corrected as shown below:

| | | |
|---|---|---|
| 5,331,015 | 7/19/94 | DesMarais et al |
| 5,336,208 | 8/9/94  | Rosenbluth et al |
| 5,336,695 | 8/9/94  | Nass et al |
| 5,352,711 | 10/4/94 | DesMarais |
| 5,387,207 | 2/7/95  | Dyer et al -- |

Signed and Sealed this

Twenty-first Day of May, 2002

Attest:

JAMES E. ROGAN
*Attesting Officer*          *Director of the United States Patent and Trademark Office*